United States Patent
Kvistgaard et al.

(10) Patent No.: US 9,956,283 B2
(45) Date of Patent: May 1, 2018

(54) MAMMALIAN MILK OSTEOPONTIN FOR ENHANCING IMMUNE RESPONSIVENESS

(71) Applicant: ARLA FOODS AMBA, Viby J (DK)

(72) Inventors: Anne Staudt Kvistgaard, Viby J (DK); Peter Langborg Wejse, Aarhus N (DK); Sharon Donovan, Champaign, IL (US); Marcia H. Monaco Siegel, Champaign, IL (US); Sarah S. Comstock, East Lansing, MI (US)

(73) Assignee: Arla Foods AMBA, Viby J (DK)

( * ) Notice: Subject to any disclaimer, the term of this patent is extended or adjusted under 35 U.S.C. 154(b) by 0 days. days.

(21) Appl. No.: 14/903,049

(22) PCT Filed: Jul. 4, 2014

(86) PCT No.: PCT/EP2014/064339
§ 371 (c)(1),
(2) Date: Jan. 5, 2016

(87) PCT Pub. No.: WO2015/001092
PCT Pub. Date: Jan. 8, 2015

(65) Prior Publication Data
US 2016/0136268 A1     May 19, 2016

Related U.S. Application Data

(60) Provisional application No. 61/843,185, filed on Jul. 5, 2013.

(30) Foreign Application Priority Data

Jul. 5, 2013   (EP) .................................... 13175267

(51) Int. Cl.
| | |
|---|---|
| *A61K 38/00* | (2006.01) |
| *A61K 38/16* | (2006.01) |
| *A61K 38/17* | (2006.01) |
| *A61K 38/18* | (2006.01) |
| *A61K 39/39* | (2006.01) |
| *A23L 33/19* | (2016.01) |
| *A61K 39/00* | (2006.01) |

(52) U.S. Cl.
CPC ............. *A61K 39/39* (2013.01); *A23L 33/19* (2016.08); *A61K 38/17* (2013.01); *A23V 2002/00* (2013.01); *A61K 2039/542* (2013.01); *A61K 2039/55* (2013.01); *A61K 2039/55516* (2013.01); *A61K 2039/575* (2013.01)

(58) Field of Classification Search
None
See application file for complete search history.

(56) References Cited

U.S. PATENT DOCUMENTS

| | | | |
|---|---|---|---|
| 7,205,398 B2 * | 4/2007 | Winslow | ................ C07K 14/52 435/170 |
| 7,259,243 B2 | 8/2007 | Sørensen et al. | |
| 2003/0220239 A1 * | 11/2003 | Simard | ................ C12N 9/0059 424/139.1 |
| 2005/0287247 A1 * | 12/2005 | Sorensen | ................ A23L 1/296 426/72 |

FOREIGN PATENT DOCUMENTS

| | | |
|---|---|---|
| WO | 98/56405 | 12/1998 |
| WO | 00/63241 | 10/2000 |
| WO | 2013/086459 | 6/2013 |

OTHER PUBLICATIONS

Albers et al., "Monitoring immune modulation by nutrition in the general population: identifying and substantiating effects on human health," British Nutrition, 2013, 110(2):1-22.
Bissonnette et al., "Proteomic analysis and immunodetection of the bovine milk osteopontin isoforms," Journal of Dairy Science, 2012, 95(2):567-579.
International Preliminary Report on Patentability for Application No. PCT/EP2014/064339 dated Oct. 9, 2015 (13 pages).
Khajoee et al., "Novel roles of osteopontin and CXC chemokine ligand 7 in the defense against mycobacterial infection," Clinical and Experimental Immunology, 2006, 143(2):260-268.
Plotkin, "Correlates of Vaccine-Induced Immunity," Vaccines, 2008, 47:401-409.
Sørensen et al., Posttranslational modifications of bovine osteopontin: Identification of twenty-eight phosphorylation and three O-glycosylation sites, Protein Science, 1995, 4:2040-2049.

* cited by examiner

*Primary Examiner* — Elizabeth C. Kemmerer
(74) *Attorney, Agent, or Firm* — Casimir Jones, S.C.; Lisa V. Mueller

(57) ABSTRACT

The disclosed invention provides mammalian milk osteopontin and/or an active truncation or active peptide thereof for improving immune responsiveness to an infectious disease in a mammal, for example a human subject, as well as enhancing the efficacy of vaccination for the prophylactic or therapeutic treatment of an infectious disease in mammals, such as humans. The invention further provides a vaccine system, for use in the prophylactic or therapeutic treatment of an infectious disease in a mammal, comprising a vaccine and a mammalian milk osteopontin and/or an active truncation or active peptide thereof for oral administration to a mammal, as well as methods of enhancing immune resistance to an infectious disease in a mammal by administration of a vaccine and a mammalian milk osteopontin and/or an active truncation thereof.

32 Claims, 18 Drawing Sheets

```
                        SEQUENCE LISTING

<160> NUMBER OF SEQ ID NOS: 1

<210> SEQ ID NO 1
<211> LENGTH: 278
<212> TYPE: PRT
<213> ORGANISM: Bos taurus
<220> FEATURE:
<221> NAME/KEY: MISC_FEATURE
<222> LOCATION: (152)..(161)
<223> OTHER INFORMATION: Motif comprising integrin binding domain

<400> SEQUENCE: 1

Met Arg Ile Ala Val Ile Cys Phe Cys Leu Leu Gly Ile Ala Ser Ala
1               5                   10                  15

Leu Pro Val Lys Pro Thr Ser Ser Gly Ser Ser Glu Glu Lys Gln Leu
            20                  25                  30

Asn Asn Lys Tyr Pro Asp Ala Val Ala Thr Trp Leu Lys Pro Asp Pro
        35                  40                  45

Ser Gln Lys Gln Thr Phe Leu Ala Pro Gln Asn Ser Val Ser Ser Glu
    50                  55                  60

Glu Thr Asp Asp Asn Lys Gln Asn Thr Leu Pro Ser Lys Ser Asn Glu
65                  70                  75                  80

Ser Pro Glu Gln Thr Asp Asp Leu Asp Asp Asp Asp Asn Ser Gln
                85                  90                  95

Asp Val Asn Ser Asn Asp Ser Asp Asp Ala Glu Thr Thr Asp Asp Pro
            100                 105                 110

Asp His Ser Asp Glu Ser His His Ser Asp Glu Ser Asp Glu Val Asp
        115                 120                 125

Phe Pro Thr Asp Ile Pro Thr Ile Ala Val Phe Thr Pro Phe Ile Pro
    130                 135                 140

Thr Glu Ser Ala Asn Asp Gly Arg Gly Asp Ser Val Ala Tyr Gly Leu
145                 150                 155                 160

Lys Ser Arg Ser Lys Lys Phe Arg Arg Ser Asn Val Gln Ser Pro Asp
                165                 170                 175

Ala Thr Glu Glu Asp Phe Thr Ser His Ile Glu Ser Glu Glu Met His
            180                 185                 190

Asp Ala Pro Lys Lys Thr Ser Gln Leu Thr Asp His Ser Lys Glu Thr
        195                 200                 205
```

```
Asn Ser Ser Glu Leu Ser Lys Glu Leu Thr Pro Lys Ala Lys Asp Lys
    210                 215                 220

Asn Lys His Ser Asn Leu Ile Glu Ser Gln Glu Asn Ser Lys Leu Ser
225                 230                 235                 240

Gln Glu Phe His Ser Leu Glu Asp Lys Leu Asp Leu Asp His Lys Ser
                245                 250                 255

Glu Glu Asp Lys His Leu Lys Ile Arg Ile Ser His Glu Leu Asp Ser
            260                 265                 270

Ala Ser Ser Glu Val Asn
            275
```

MAMMALIAN MILK OSTEOPONTIN FOR ENHANCING IMMUNE RESPONSIVENESS

CROSS-REFERENCE TO RELATED APPLICATIONS

This is a U.S. national stage entry of International Patent Application No. PCT/EP2014/064339, filed on Jul. 4, 2014, which claims priority to European Patent Application No. 13175267.7, filed on Jul. 5, 2013 and U.S. Patent Application No. 61/843,185, filed on Jul. 5, 2013, the entire contents of all of which are fully incorporated herein by reference.

FIELD OF THE INVENTION

The present invention relates to improving immune responsiveness to an infectious disease in a mammal, for example a human subject, as well as enhancing the efficacy of vaccination for the prophylactic or therapeutic treatment of an infectious disease in mammals, such as humans. Oral administration of mammalian milk osteopontin (OPN), or an active truncated portion thereof, has been found to enhance the immune responsiveness of a mammal, and to enhance the immune response induced by vaccination in a mammal, thereby enhancing the prophylactic or therapeutic efficacy of the vaccination.

BACKGROUND OF THE INVENTION

The immune system provides the primary mechanism of defense against disease in living organisms, whereby pathogens and foreign organisms are detected and eliminated by components of the immune system. The innate immune response functions as the first line of defense against infection, comprising diverse cellular components including granulocytes (basophils, eosinophils and neutrophils), mast cells, natural killer cells (NKC) and antigen presenting cells (APCs), such as macrophages and dendritic cells (DC) and soluble factors, such as complement proteins. The adaptive immune response as the second line defense is slower to develop, and includes the selection of cellular versus humoral responses for the elimination of pathogens. Cellular immunity is primarily Th1-induced, leading to the differentiation of cytotoxic T-cells, natural killer cells (NKC) and activated macrophages that serve to destroy compromised host cells (e.g. virus or pathogen infected cells). Humoral immunity manifests as increased antigenic specificity and antigen memory, whereby Th2 activation and cytokine production leads to the generation of B cells producing antibodies and memory cells that facilitate the recognition of pathogen-derived antigens and pathogen elimination.

The innate immunity in the newborn mammal is underdeveloped, such that disease resistance in the newborn depends heavily on the passive acquisition of maternal antibodies received through maternal breast milk, in particular colostrum. In parallel, development of the infant immune system is induced by immune-stimulating components present in the maternal milk. Development of the immune system in newborn mammals fed formula milk rather than maternal milk is delayed due to a deficiency of the major immunity-inducing and -conferring components that would otherwise be provided in maternal milk.

Maintenance of the immune system remains essential for health throughout life, and thus immune-compromised individuals of any age, as well as elderly individuals with a steadily declining immunity, represent patient groups at greater risk of disease-related mortality.

Vaccination to raise immune resistance to infectious diseases is the most effective method of improving public health. The range of diseases for which vaccines are available is increasing continually, and the use of these vaccines to protect the adult population, in particular the growing elderly population is increasing. Vaccination, either prophylactic or therapeutic, stimulates the body's immune system to recognize an antigenic agent resembling a given disease-causing agent; to destroy it; and "remember" it, so that the immune system can more easily recognize and destroy the disease-causing agent upon reexposure. Typically such an agent is made from weakened or killed forms of the pathogenic microbe, its toxins or one of its surface proteins.

Since the efficacy of vaccination depends on the ability of the vaccinated subject to raise an effective immune response, the benefits of vaccination are reduced in individuals in which the immune system is either not fully developed, as in new-born or young infants, or individuals in whom the immune system is either reduced, compromised or in decline, as in some adults and the elderly. Accordingly, there exists a need for agents that can enhance the immune responsiveness in these patient groups, in particular their immune response to vaccination. Public health programs to vaccinate these large patient populations must be extremely safe and, hence, both the agents used to enhance the immune response to vaccination and the means used for their administration must meet these safety requirements.

Osteopontin (OPN) is an extracellular matrix protein expressed by a number of cell types including osteoclasts, osteoblasts, macrophages, activated T-cells, smooth muscle cells and epithelial cells. It is present in several tissues including bone, kidney, placenta, smooth muscle and secretory epithelia. OPN is able to mediate cell adhesion and migration, and is associated with normal tissue remodeling processes such as bone resorption, angiogenesis, wound-healing and tissue injury. OPN is also expressed in certain diseased states e.g. restenosis, atherosclerosis, renal diseases and tumorigenesis. Modified transcription of the gene encoding OPN has been observed, wherein alternative splice transcripts lead to expression of different forms of OPN in certain disease states (Bissonnette et al 2012). OPN exerts many of its biological effects by interacting with integrins, which comprise a large family of heterodimeric transmembrane receptors that mediate both cell-cell and cell-matrix interactions, and may play a role in inflammatory diseases.

WO 98/56405 A1 relates to a method of modulating (augmenting or reducing) an individual's immune response by altering (increasing or decreasing) osteopontin activity; but lacks evidence to support a therapeutic effect of administering OPN (e.g. recombinant OPN) to a subject.

WO 00/63241 A2 relates to Eta-1/osteopontin as a regulator of immune responses; but fails to evidence that administration of OPN enhances immune resistance to infectious disease.

Khajoee V et al., 2006 CLINICAL AND EXPERIMENTAL IMMUNOLOGY, 143(2):260-268; relates to the role of osteopontin in defense against mycobacterial infection; based on studies conducted with human monocyte-derived macrophage cell cultures.

SUMMARY OF THE INVENTION

Figure 1:
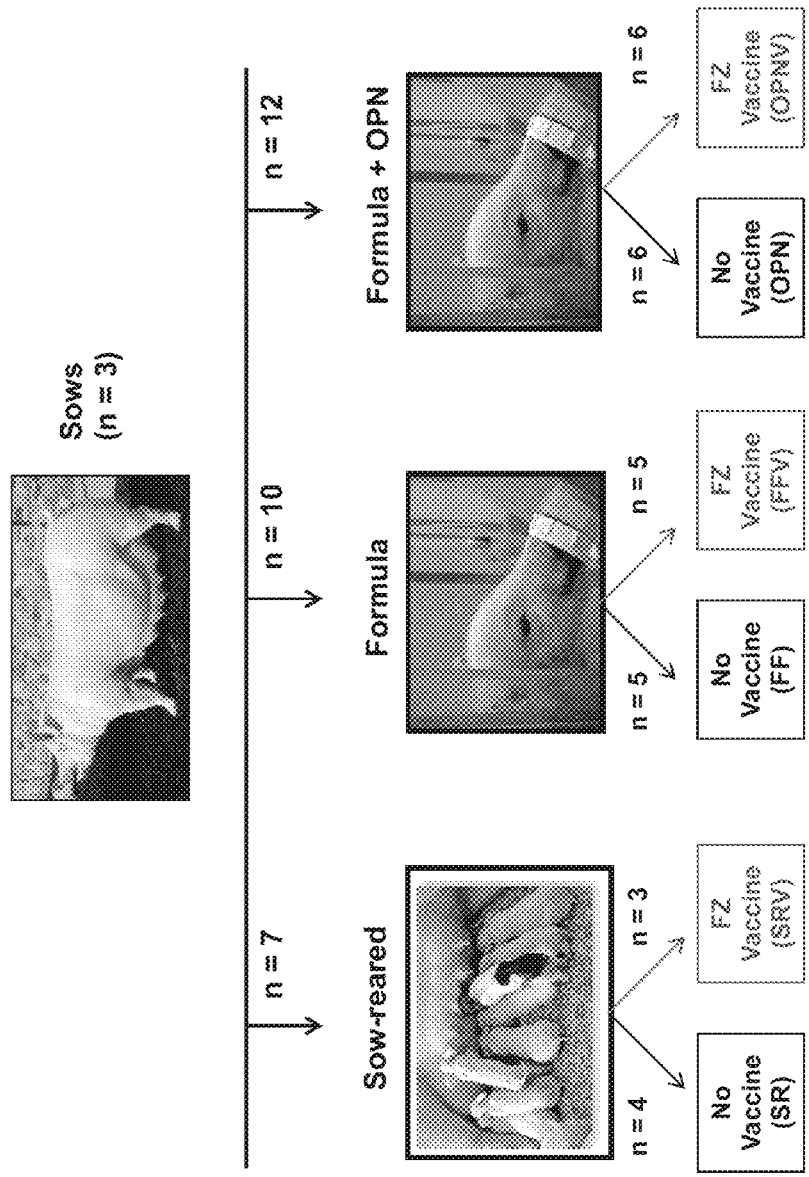
FIG. 1 Animal test population and study design. Piglets were divided into three dietary groups receiving either a sow milk replacer formula (FF; n=10) or formula supplemented with 140 mg/L osteopontin (OPN; n=12), or were sow-reared (SR; n=7).

Mammalian milk osteopontin (OPN) and/or an active truncation thereof, when administered orally, have unexpectedly been found to enhance the specific immune responsiveness in a mammalian subject, and thereby improve their specific immune response to vaccination. The invention is based on the first study to document that oral administration of OPN can be used to enhance the specific immune responsiveness induced in a mammalian subject by vaccination.

The invention provides mammalian milk OPN and/or an active truncation thereof for use as a medicament for enhancing immune resistance to an infectious disease in a mammal, for example by enhancing immune resistance induced by vaccination against the disease, wherein the OPN and/or the active truncation thereof is for oral administration. According to one embodiment, the active truncated OPN comprises at least one active OPN peptide derivable from mammalian milk OPN by proteolytic cleavage. The OPN or an active truncation thereof may be used for oral administration either prior to; concurrently with; or subsequent to vaccination of the mammal, or a combination thereof.

The mammalian milk OPN and/or an active truncation thereof are capable of strengthening the humoral immunity in the mammal.

The mammalian milk OPN and/or an active truncation thereof can be derived from any one of bovine, goat, sheep, camel, buffalo, dromedary, llama and any combination thereof.

According to one embodiment, the mammalian milk OPN and/or the active truncation thereof, is for use in enhancing immune resistance to an infectious disease in a mammal, where the mammal is a human. According to one embodiment, the human belongs to an age group selected from among 0-5, 6-11, 12-18, 19-34, 35-44, 45-54, 55-64, 65-74, 75-84, and older than 84 years of age.

According to one embodiment, the infectious disease is selected from among influenza; diphtheria, tetanus, whooping cough, polio, measles, mumps and rubella, tuberculosis, hepatitis B, meningitis C; human papilloma virus; rotavirus; influenza type a, influenza type b, pneumococcal infection and shingles.

The invention further provides a vaccine system comprising a vaccine and a mammalian milk OPN and/or an active truncation thereof for use in the prophylactic or therapeutic treatment of an infectious disease in a mammal, wherein the mammalian milk OPN and/or an active truncation is for oral administration, for example either prior to; concurrently with; or subsequent to vaccination of the mammal, or a combination thereof. Oral administration of the mammalian milk OPN and/or an active truncation enhances the immune resistance to an infectious disease in a mammal induced by vaccination. The mammalian milk osteopontin and/or the active truncation are capable of strengthening the humoral immunity in the vaccinated.

According to one embodiment, the vaccine system comprises OPN and/or the active truncation thereof derived from bovine, goat, sheep, camel, buffalo, dromedary, llama, or any combination thereof.

According to one embodiment of the vaccine system, the mammal is a human.

According to one embodiment of the vaccine system, the infectious disease is selected from among influenza, diphtheria, tetanus, whooping cough, polio, measles, mumps and rubella, tuberculosis, hepatitis B, meningitis C, rotavirus, human papilloma virus, influenza type a, influenza type b, pneumococcal infection and shingles.

According to one embodiment of the vaccine system, the vaccine is selected from among diphtheria vaccine, tetanus vaccine, whooping cough vaccine, polio vaccine, or a combined vaccine (e.g. TaP/IPV vaccine); a combined measles, mumps and rubella vaccine (e.g. MMR vaccine); tuberculosis vaccine (e.g. BCG vaccine); hepatitis B vaccine; meningitis C vaccine); rotavirus (rotavirus vaccine); Human Papilloma Virus (HPV) vaccine; Influenza type a and type b vaccine (e.g. Flu vaccine); Pneumococcal vaccine; and Herpes zoster vaccine.

According to one embodiment of the vaccine system, the human belongs to an age group selected from among 0-5, 6-11, 12-18, 19-34, 35-44, 45-54, 55-64, 65-74, 75-84, and older than 84 years of age.

The invention further provides a method of enhancing immune resistance to an infectious disease in a mammal, comprising administering a vaccine and mammalian milk OPN and/or one or more active truncation thereof to the mammal, wherein the OPN and/or the active truncation thereof is administered orally. The mammalian milk OPN and/or the active truncation are capable of strengthening the humoral immunity in the vaccinated mammal.

According to one embodiment of the method of enhancing immune resistance to an infectious disease in a mammal, the mammal is a human.

According to one embodiment of the method, the OPN or an active truncation thereof is administered prior to; concurrently with; or subsequent to vaccination of the mammal, or a combination thereof.

According to one embodiment of the method, the OPN or an active truncation thereof is administered in a daily dosage in the range of about 0.05 mg/kg of body weight to about 5 g/kg of body weight of the subject treated.

According to one embodiment of the method of enhancing immune resistance to an infectious disease in a human, the human belongs to an age group selected from among 0-5, 6-11, 12-18, 19-34, 35-44, 45-54, 55-64, 65-74, 75-84, and older than 84 years of age.

According to one embodiment of the method, the OPN or an active truncation thereof is of mammalian origin, selected from bovine, goat, sheep, camel, buffalo, dromedary, llama and any combination thereof.

According to one embodiment of the method, the infectious disease is selected from among influenza, diphtheria, tetanus, whooping cough, polio, measles, mumps and rubella, tuberculosis, hepatitis B, meningitis C, rotavirus, human papilloma virus; influenza type a, influenza type b, pneumococcal infection and shingles.

According to one embodiment of the method, the vaccine is selected from among diphtheria vaccine, tetanus vaccine, whooping cough vaccine, polio vaccine, or a combined vaccine (e.g. TaP/IPV vaccine); a combined measles, mumps and rubella vaccine (e.g. MMR vaccine); tuberculosis vaccine (e.g. BCG vaccine); hepatitis B vaccine; meningitis C vaccine); rotavirus (rotavirus vaccine); Human Papilloma Virus (HPV) vaccine; influenza type a and type b vaccine (e.g. Flu vaccine); Pneumococcal vaccine; and Herpes zoster vaccine.

DETAILED DESCRIPTION OF THE INVENTION

The present invention addresses the need to enhance the immune response in mammalian subjects, in particular formula fed babies and infants; adults with a reduced immune capacity (e.g. immune-compromised subjects); and the elderly. The inventors have found that mammalian milk OPN and/or an active truncation thereof, when administered orally to a subject, enhances the immune responsiveness in the mammal thereby improving the efficacy of vaccination of the mammal.

I Mammalian Milk Osteopontin (OPN) and/or an Active Truncation Thereof
I. i Structure of Mammalian Milk OPN According to a first embodiment, the invention provides mammalian milk OPN and/or an active truncation thereof for use in enhancing immune responsiveness to infectious diseases, and in particular vaccine-induced immune resistance to an infectious disease in a mammal.

Mammalian milk OPN is a soluble milk protein produced by secretion from the mammary gland. While mammalian milk OPN is secreted as a polypeptide having a molecular mass of approximately 60 kDa (as determined by SDS-PAGE), it is commonly found to co-exist in milk with truncated forms of OPN. In contrast to alternative (transcription), spliced OPN isoforms expressed in other tissues, mammary milk OPN is present in only one spliced isoform; while the truncated forms of milk OPN are the result of proteolytic cleavage of this secreted polypeptide isoform. Milk OPN, both the full-length polypeptide and truncated forms thereof, are highly phosphorylated and glycosylated polypeptides. The posttranslational pattern of phosphorylation and glycosylation of OPN is known to be tissue specific and to regulate its physiological properties. The high level and pattern of phosphorylation and glycosylation of milk OPN polypeptide isoforms is a distinguishing feature important for its functional properties (Bissonnette et al 2012).

The milk OPN, according to the invention is of mammalian origin, and may be derived, for example, from bovine, goat, sheep, camel, buffalo, dromedary or llama milk. Milk OPN polypeptide comprises a number of highly conserved sequence motifs, in particular an RGD motif, characterized by alfa-integrin binding properties. The location of these motifs, conserved amongst mammalian milk OPN polypeptides, is identified with respect bovine OPN, whose primary translation product amino acid sequence is set out in Table 1.

TABLE 1

Amino add sequence of
bovine OPN [SEQ ID NO 1]

```
         10          20          30          40
MRIAVICFCL  LGIASALPVK  PTSSGSSEEK  QLNNKYPDAV 50          60          70          80
ATWLKPDPSQ  KQTFLAPQNS  VSSEETDDNK  QNTLPSKSNE 90         100         110         120
SPEQTDDLDD  DDDNSQDVNS  NDSDDAETTD  DPDHSDESHH 130         140         150         160
SDESDEVDFP  TDIPTIAVFT  PFIPTESAND  GRGDSVAYGL 170         180         190         200
KSRSKKFRRS  NVQSPDATEE  DFTSHIESEE  MHDAPKKTSQ 210         220         230         240
LTDHSKETNS  SELSKELTPK  AKDKNKHSNL  IESQENSKLS 250         260         270
QEFHSLEDKL  DLDHKSEEDK  HLKIRISHEL  DSASSEVN
```

UniProtKB: P31096
Signal peptide: amino acids 1-16
Mature full-length OPN: amino acids 17-278
* = $R^{163}/S^{164}$ predicted thrombin cleavage site and putative in vivo truncation cleavage site
FPTDIPT and RGDSVAYGLK motifs (underlined sequence): predicted integrin binding sites
Phosphorylation sites*: T or S residues underlined and italics
O-glycosylation sites*: T residues in bold
*Sorensen et al 1995

When the mammalian milk OPN is derived from bovine milk, the OPN typically comprises at least one active truncated OPN polypeptide in addition to mature full-length OPN polypeptide. Typically, the one or more active truncated OPN polypeptides has a molecular mass of approximately 40 kDa (as determined by SDS-PAGE). Typically, the one or more active truncated OPN polypeptides are derived from the full-length OPN polypeptide by in vivo peptide bond cleavage at a position that is C-terminal to the RGD motif. Typically, the at least one or more active truncated bovine milk OPN is derived from a full-length mature OPN polypeptide, where the mature OPN has an amino acid sequence having a determined sequence identity to residues 17-278 of SEQ ID NO: 1. Bovine milk OPN is a secreted polypeptide, having a signal peptide (corresponding to amino acid residues 1-16 of SEQ ID NO: 1) that is co-translationally removed to yield a mature full-length polypeptide. When the bovine milk OPN comprises a full-length OPN polypeptide, it typically has an amino acid sequence of residues 17-278 of SEQ ID NO: 1. One active truncated bovine milk OPN is predicted to be derived from bovine OPN polypeptide (SEQ ID NO: 1) by peptide cleavage at or close to the thrombin cleavage site (Table 1), yielding a C-terminally truncated OPN polypeptide having a molecular mass of approximately 40 kDa (as determined by SDS-PAGE) that retains the RGD motif.

According to one embodiment, the mammalian milk OPN comprises a mature full-length OPN polypeptide having at least 66, 68, 70, 72, 74, 76, 78, 80, 82, 84, 88, 90, 92, 94, 96, 98, 100% amino acid sequence identity to SEQ ID NO: 1; and/or one or more active truncated OPN polypeptide having at least 66, 68, 70, 72, 74, 76, 78, 80, 82, 84, 88, 90, 92, 94, 96, 98, 100% amino acid sequence identity to a polypeptide having the sequence selected from among any one of amino acid residues 17-161; 17-162; 17-163; 17-164 and 17-165 of SEQ ID NO: 1.

In the context of the present invention, the term "sequence identity" relates to a quantitative measure of the degree of identity between two amino acid sequences or between two nucleic acid sequences, preferably of equal length. If the two sequences to be compared are not of equal length, they must be aligned to the best possible fit. The sequence identity can be calculated as (Nref−Ndif)*100)/(Nref), wherein Ndif is the total number of non-identical residues in the two sequences when aligned, and wherein Nref is the number of residues of the reference sequences. Hence, the DNA sequence AGTCAGTC will have a sequence identity of 75% with the sequence AATCAATC (Ndif=2 and Nref=8). A gap is counted as non-identity of the specific residue(s), i.e. the DNA sequence AGTGTC will have a sequence identity of 75% with the DNA sequence AGTCAGTC (Ndif=2 and Nref=8). Sequence identity can for example be calculated using appropriate BLAST-programs, such as the BLASTp-algorithm provided by National Center for Biotechnology Information (NCBI), USA The mammalian milk OPN may comprise active truncated OPN polypeptide (tOPN) or full-length OPN polypeptide (flOPN), or the two forms may be present in various ratios. For example the ratio of tOPN/flOPN may range from between 0:100 to 100:0; more preferably the ratio is any one of 5:95; 10:90; 15:85; 20:80; 25:75; 30:70; 35:65; 40:60; 45:55; 50:50; 55:45; 60:40; 65:35; 70:30; 75:35; 80:20; 85:15; 90:10; and 95:5. Typically the ratio in bovine milk is 75% tOPN to 25% flOPN, where the tOPN has a molecular mass of approximately 40 kDa (as determined by SDS-PAGE).

According to a further embodiment, the mammalian milk OPN is a truncated OPN, where the truncated OPN comprises at least one active OPN peptide derivable from mammalian milk OPN (for example bovine milk OPN having SEQ ID No. 1) by proteolytic cleavage. Mammalian OPN, during passage through the digestive tract of a mammalian subject, is exposed to proteolytic enzymes, in particular the endoproteases pepsin, trypsin, and chymotrypsin. Active OPN peptides, according to the present invention, are peptides that retain activity subsequent to exposure to proteases typically present in the digestive tract of a mammal. Active OPN peptides may typically include peptides comprising part or all of the integrin-binding motifs, typically having a length of from 5 to 16 amino acid residues.

I. ii Mammalian Milk OPN Enhances Specific Immune Responses Induced in a Mammal by Vaccination The mammalian milk OPN according to the invention comprises full-length OPN polypeptide (flOPN) and/or at least one active truncated OPN polypeptide or peptide (tOPN) that is capable of enhancing the immune responsiveness of a mammal, and thereby increasing the specific immune response induced in a mammal by exposure to (and optionally infected with) an infectious disease or by vaccination. A specific immune response in a mammal exposed to (infected) by an infectious disease or in a vaccinated mammal comprises the production of a population of antibody molecules that selectively react with the antigen present in the agent of the infectious disease (examples of infectious diseases and their agents is detailed in II i) or in the vaccine. The term "active" in respect of a truncated OPN polypeptide or peptide of the present invention is defined as the capability of enhancing the specific immune response of a mammal to an infectious disease or to vaccination.

The titer of specific antibodies induced by vaccination is commonly used as an in vivo indicator of the integrated immune response upon vaccination; as well as being an indicator of the clinical protection that may be conferred that is specific for a given vaccine (Albers et al. 2013).

The effect of administering bovine milk OPN on the specific immune response induced in a mammal by vaccination is exemplified in Example 1. In this example, piglets fed on a formula diet supplemented with bovine milk OPN, responded to Fluzone vaccine, by producing Fluzone-specific IgGs over a period of 21 days, whose titer in piglet serum samples was significantly higher than serum from control formula fed piglets, while matching the IgG levels seen in piglets receiving swine milk that contains native swine OPN.

A specific immune response in a vaccinated mammal can be determined by directly or indirectly detecting and quantitating the antibodies present in a sample of body fluid derived from the mammal that can form a complex with the vaccine antigen(s). Where the vaccine is particulate, for example a whole-cell inactivated vaccine, a quantitative agglutination (cell clumping) test can be used to determine the serial dilution of the body fluid sample that contains sufficient specific antibodies to induce cell clumping of the whole-cell vaccine. When the vaccine is soluble, for example a protein subunit or peptide vaccine, an Enzyme Linked Immunosorbent Assay (ELISA) is a suitable method for specific antibody detection. The use of the ELISA method for antibody detection is illustrated in Example 1.3, where Fluzone vaccine specific IgG antibodies are detected using an ELISA assay specific for pig.

I. iii Mammalian Milk OPN Enhances the Humoral Immune Responsiveness of a Mammal Surprisingly, oral administration of OPN, for example in the form of an OPN-supplement to the diet, induces a strong stimulation of humoral immunity, such as to provide enhanced levels of antigen specific IgGs in vaccinated mammals and a generally higher level of IgG. This is exemplified in Example 1, where piglets receiving an OPN-supplemented formula diet are compared with piglets on a formula diet or sow-reared. The cause of this response is believed to lie in a number of modifications of the immune system seen in piglets receiving an OPN-formula diet. Firstly, piglets receiving an OPN-supplemented diet have elevated levels of IL-10 when compared to control formula-fed or sow-reared piglets, which contributes to the induction of a Th2 response and stimulates the differentiation of B cells into antibody-secreting cells leading to the higher IgG levels. The OPN-induced production of IL-10 also plays a key role in inhibiting down-stream Th1-responses such as macrophage activation and pro-inflammatory responses.

Secondly the elevated levels of IL-12 found in serum of OPN-formula fed piglets would stimulate differentiation of Th1 cells which in turn would lead to the activation of the differentiated B cells, inducing them to secrete antibodies (IgGs). The induction of this humoral response in piglets receiving an OPN-supplemented diet is reflected in the significantly elevated levels of CD4 secreting T helper cells and relatively lower levels of CD8 secreting cytotoxic T cells, when compared to the lymphocyte profile of cells derived from formula fed or sow reared piglets. The T helper cell population, via the Th1 and Th2 systems contributes to the observed humoral response and importantly the enhanced levels of antigen specific IgG following vaccination. In the case of infant piglets raised on formula diet, the addition of OPN to the diet improves the vaccination response to levels seen in swine-fed piglets. These studies provide evidence that the addition of OPN to the diet has the capacity to enhance and boost the immune response to vaccination, and thereby improve the immunity to the antigen in the administered vaccine. This conclusion is supported by the fact that the titer of antibodies induced by vaccination is at least a relative correlate of protection against the disease conferred by the vaccination (Plotkin, S A., 2008).

I iv Mammalian Milk OPN Enhances Immune Resistance to an Infectious Disease in a Mammal Oral administration of mammalian milk OPN, according to the invention, to mammals, in particular human infants, enhances their immune resistance to infectious diseases. This is clearly demonstrated in the clinical trial described in Example 2, where the frequency of infectious events was monitored by measuring and detecting elevated body temperature (pyrexia) in an infant as a diagnostic symptom of an infectious disease contracted by the infant that is caused by an infectious agent (e.g. viral, bacterial, fungal or eukaryotic pathogenic agent such as a protozoan infection).

I v Preparation of Mammalian Milk OPN Suitable for Administration

Mammalian milk OPN, that is present in milk of a lactating mammal, may be purified to provide an enriched source of OPN, which may be at least about 50% to about 60%, at least about 60% to about 70%, or at least about 70% to about 80% pure. In some embodiments, it is at least about 80% to about 90% pure, while in other embodiments, the source of milk OPN is at least about 90% to about 95% pure, or more. In certain embodiments, the purified source of milk OPN is at least about 95% pure, such as 95%, 96%, 97%, 98%, 99%, or 99.5% pure, or more.

In specific embodiments, the source of the OPN is a purified bovine milk OPN preparation, such as for example Lacprodan OPN-10® (Aria Foods Ingredients, Viby, Denmark) (see also U.S. Pat. No. 7,259,243). Lacprodan OPN-10® comprises approximately 22% (w/w) full length bovine milk OPN and approximately 65% (w/w) of a bovine milk OPN isoform (a truncated OPN).

I vi Formulation and Dosage of Mammalian Milk OPN

The mammalian milk OPN according to the invention, for example bovine milk OPN, may be administered in a daily dosage in the range of about 0.05 mg/kg of body weight to about 5 g/kg of body weight of the subject treated. For infants, the daily OPN dosage is typically in the range of about 5-50 mg/kg body weight preferably 25-50 mg/kg body weight for infants having a body weight in the weight range of 3 to 10 kg. Typically, it is recommended to administer 0.5-5 g OPN per day for an adult, for example in a daily dosage volume of 100-250 ml. The dosage form may contain mammalian milk OPN in the range of 0.1 mg-10 g per dosage form. For example, the oral dosage form may contain an amount of the OPN in the range of 1 mg-1 g per dosage form. Alternatively, the oral dosage form may contain an amount of the OPN in the range of 10 mg-800 mg per dosage form. The oral dosage form may e.g. contain an amount of the OPN in the range of 25 mg-500 mg per dosage form.

The mammalian milk OPN may be administered in the form of a nutritional supplement, where the supplement comprises the milk OPN in an amount in the range of 0.01-90% (w/w). For example, the nutritional supplement may comprise the milk OPN in an amount in the range of 0.1-80% (w/w). Alternatively, the nutritional supplement may comprise the milk OPN in an amount in the range of 1-70% (w/w).

In some embodiments of the invention the nutritional supplement comprises the milk OPN in an amount in the range of 5-60% (w/w). For example, the nutritional supplement may comprise the milk OPN in an amount in the range of 10-50% (w/w). Alternatively, the nutritional supplement may comprise the milk OPN in an amount in the range of 0.1-20% (w/w).

In other embodiments of the invention the nutritional supplement comprises the milk OPN in an amount in the range of 0.001-5% (w/w). For example, the nutritional supplement may comprise the milk OPN in an amount in the range of 0.005-2% (w/w). Alternatively, the nutritional supplement may comprise the milk OPN in an amount in the range of 0.01-1% (w/w). The nutritional supplement may e.g. comprise the milk OPN in an amount in the range of 0.05-0.5% (w/w). Typically, a ready-to-drink nutritional beverage comprises milk OPN in an amount in the range of 0.005% to 0.05% (w/w).

Nutritional supplements comprising the milk OPN can be pre-packaged in liquid or powdered form (for example canned or bottled liquid drink). In some embodiments, the powdered form is added to a food or beverage to provide additional nutrients. In certain embodiments, the nutritional beverages are formulated with, for example, fruit, vegetables, yogurt, milk, and/or ice cream. In some embodiments, the nutritional supplements are blended to a smoothie consistency. In particular embodiments, the nutritional beverages are fortified with, for example, protein, vitamins, minerals, antioxidants, probiotics, and/or prebiotics. In certain embodiments, the nutritional beverages are lactose-free and/or gluten-free. In some embodiments, the nutritional supplements are organic. Examples of pediatric nutritional beverages include PEDIASURE®, PEDIASMART®, and RESOURCE® Just For Kids. Examples of adult nutritional beverages include ENSURE®, BOOST®, NESTLE® CARNATION® INSTANT BREAKFAST®, GLUCERNA®, GLYTROL®, NUTREN®, and PEPTAMEN®. Nutritional supplements also include milk, both soymilk and cow's milk (for example whole, semi-skim or low-fat, skim or non-fat (for example Cravendale), lactose-free (for example LACTOFREE®).

I vii Administration of Mammalian Milk OPN

Mammalian milk OPN, formulated for oral administration to a mammal (including nutritional supplements or beverages comprising mammalian milk OPN) as described in I v, may be administered to a mammal either prior to, concurrently to, or subsequent to vaccination, or a combination thereof. Preferably, oral administration of the milk OPN is initiated prior to vaccination and the administration is continued at least until the vaccination is administered. Where administration of milk OPN is initiated prior to vaccination, it is preferable that administration is initiated at least 1-21 days prior to vaccination, typically at least 1-7 days prior to vaccination, and is continued at least until the vaccination is administered. Advantageously, the period of administration of milk OPN may be further extended following vaccination for at least an additional 1-4 weeks. If vaccination of the mammal includes a booster vaccination the period of administration of milk OPN (or formulations thereof) is preferably extended to at least the delivery of the booster vaccine.

II Vaccines

II. i Vaccines for Prophylactic and Therapeutic Treatment of Mammals

Vaccines can serve both prophylactic and therapeutic functions, whereby prophylactic or therapeutic treatment can be used to increase immune resistance to an infectious disease in a mammal and thereby lower the risk of infection or treat an existing infection.

According to one embodiment the vaccine is used to increase immune resistance to an infectious disease, where the vaccine comprises an immunogen capable of inducing an immunogenic response in a mammalian subject. The immunogen may comprise a suspension of a live (preferably attenuated) or killed infectious agent (for example a microorganism such as a bacterium or virus, a parasite, or other pathogen) that causes an infectious disease. Alternatively, the immunogen may comprise an immunogenic polypeptide, for example a polypeptide derived from an infectious agent which may be an antigen and which therefore activates an immune response in an animal. In other embodiments, the immunogen may be a nucleic acid, such as a recombinant vector (including DNA vectors or plasmids, retroviral vectors and lentivirus vectors) that encodes an antigen and may be administered, e.g., as part of a DNA vaccine.

In one embodiment, the immunogen is derived from a pathogen selected from among viral, bacterial, fungal, or protozoan pathogens of mammals (e.g. humans). Infectious diseases to be treated by a vaccine according to the invention include diphtheria, tetanus, whooping cough and polio (typically treated by a combined vaccine e.g. TaP/IPV vaccine; MMR: measles, mumps and rubella (e.g. MMR vaccine); tuberculosis (e.g. BCG vaccine); hepatitis B (e.g. Hepatitis B vaccine); meningitis C (e.g. Meningitis C vaccine); Human Papilloma Virus (HPV) as the causal agent for cervical/anal cancer and genital warts (e.g. HPV vaccine); influenza type a and type b (e.g. Flu vaccine); pneumococcal infection Pneumococcal vaccine); rotavirus (rotavirus vaccine) and shingles (Herpes zoster vaccine). Vaccination against shingles is largely limited to the elderly, while vaccination against all the other listed diseases is relevant for all age groups, although vaccination is primarily administered during early childhood.

II ii Formulation of a Vaccine for Prophylactic and Therapeutic Treatment

A vaccine generally comprises a therapeutically effective dose of an immunogen (e.g., an antigen of an infectious agent, tumor antigen, fixed tumor cells) and, preferably, an adjuvant and/or a pharmaceutically acceptable carrier. The term "adjuvant" refers to a compound or mixture that enhances the immune response to an antigen. An adjuvant can serve, e.g., as a tissue depot that slowly releases the antigen, and also as a lymphoid system activator that enhances the immune response 10 (see Hood et al., Immunology, Second Ed., 1984, Benjamin/Cummings: Menlo Park, Calif., p. 384). Exemplary adjuvants include, but are not limited to, Freund's adjuvant (complete and incomplete), saponin, mineral gels such as aluminum hydroxide, aluminum phosphate, surface active substances (for example, lysolecithin), pluronic polyols (e.g. Carbopol), polyanions, polypeptides (e.g. bovine serum albumin, ovalbumin), oil or hydrocarbon emulsions (e.g. mannide mono-oleate (Aracel A)), keyhole limpet hemocyanins, dinitrophenol, and potentially useful human adjuvants such as BCG (Bacille Calmette-Guerin) and *Corynebacterium parvum*.

II iii Immunization Protocol and Dosage

The vaccines are administered in a manner compatible with the dosage formulation, and in such frequency and amount as will be prophylactic or therapeutically effective and immunogenic. The vaccine will typically be administered as a pre-infection vaccine, but can be given as post-infection vaccine. According to one embodiment a standard immunization protocol comprises a primary vaccination that may be followed by one or more booster vaccinations administered 1, 2, 3, 4, 5, 6, 7, 8 or more weeks later. The quantity to be administered depends on the age and weight of the subject to be treated, including, e.g., the capacity of the individual's immune system to mount an immune response, and the degree of protection desired. Suitable dosage ranges are of the order of several hundred micrograms of the polypeptides of the single or multi-stage subunit vaccine per vaccination with a preferred range from about 0.1 µg to 1000 µg, such as in the range from about 1 µg to 300 µg, and especially in the range from about 4 µg to 100 µg.

II iv Administration of a Vaccine

Any of the conventional methods for administration of a vaccine are applicable, including oral, nasal or mucosal administration in either a solid form containing the active ingredients (such as a pill, suppository or capsule) or in a physiologically acceptable dispersion, such as a spray, powder or liquid, or parenterally, by injection, for example, subcutaneously, intradermally or intramuscularly or transdermally applied.

Vaccine formulations suitable for administration as suppositories include traditional binders and carriers (e.g. pregelatinised maize starch, polyalkalene glycols or triglycerides); such suppositories may be formed from mixtures containing the active ingredient in the range of 0.5% to 10%, preferably 1-2%. Oral formulations include such normally employed excipients as, for example, pharmaceutical grade mannitol, lactose, starch, magnesium stearate, sodium saccharine, cellulose, magnesium carbonate, and the like. These compositions take the form of solutions, suspensions, tablets, pills, capsules, sustained release formulations or powders and advantageously contain 10-95% of active ingredient, preferably 25-70%.

III Population Groups Responsive to the Oral Administration of Mammalian Milk OPN The present invention is directed to the oral administration of mammalian milk OPN to enhance the specific immune response induced in a mammal by exposure to (and optionally infected with) an infectious disease or by vaccination. The mammal may be a selected from among porcine, ruminant, equine, feline, canine, and a primate. Preferably the mammal is a human subject. Population groups for which the oral administration of mammalian milk OPN is particularly beneficial are the new born or young infants, particularly during the period of vaccination of childhood diseases (see Iii); as well as individuals having an immune system that is either reduced, compromised or in decline, as in the case of some adults and the elderly. The human subject belongs to these population groups may be selected from individuals belonging to age groups 0-5, 6-11, 12-18, 19-34, 35-44, 45-54, 55-64, 65-74, 75-84, and older than 84 years of age.

Example 1

1. Protocol
1.1 Animal Test Population and Study Design

Pregnant sows (~day 84 of gestation; n=3) that had not previously been vaccinated were obtained from Midwest Research Swine (Gibson, Minn.). Blood samples were taken from the sows to test for FZ-specific IgG by ELISA assay (FZ is the human influenza vaccine Fluzone™). Sows with the lowest FZ-specific IgG titers were selected for the study. Upon receipt, the selected sows were vaccinated with Utter-Guard LT-C (*Clostridium perfringens* Type C and *Escherichia coli* Bacterin-Toxoid; Pfizer Animal Health, Exton, Pa.), RespiSure1 One (*Mycoplasma hyopneumoniae* Bacterin; Pfizer), and Rhinogen BPE (*Bordotella bronchiseptica, Erysipelothrix rhusiopathiae, Pateurella multocida* Bacterin-toxoid; Intervet Inc., Millsboro, Del.), followed by a booster vaccination 2 weeks prior to farrowing. The sows did not receive vaccination against swine influenza virus (SIV). The sows were housed in farrowing crates and placed on gestation diet enriched with an antibiotic (BMD). Sows were allowed to farrow naturally and piglets received colostrum for 4 hours postpartum, within which period the piglets take up antibodies present in the sow's colostrum and acquire passive immunity to common infections to which the sows were vaccinated.

1.2 Animal Diet Groups and Vaccination Program

Piglets were then randomized to three dietary groups, receiving either a sow milk replacer formula (FF; n=10) or formula supplemented with 140 mg/L bovine milk OPN (Lacprodan OPN-10 supplied by Aria Food Ingredients Group I/S, Sønderhøj 10-12, 8260 Viby J, Denmark) (OPN; n=12) (sow milk replacer formula is LiquiWean obtained from, Milk Specialties, Dundee, Ill.), while the third group of piglets (n=7) were sow-reared (SR) and served as the reference group (FIG. 1). FF and OPN piglets were individually-housed in customized cages in environmentally controlled rooms (25° C.). The sow milk replacer formula (based on cow milk protein) was prepared daily and offered 22-times at a rate of 360 mL/kg/d.

On day 7, half of the piglets in each dietary group (SR, FF, OPN) were vaccinated (SRV, FFV, OPNV) with a 0.25 mL intra muscular injection of human influenza vaccine (Fluzone™, Sanofi Pasteur, Swiftwater, Pa.). The vaccinated piglets received a booster vaccination (at an equal dose as the first vaccination) on day 14.

1.3 Analysis of Serum Antibody Concentrations in Serum Derived from Blood Samples Blood samples were collected on day 7 (baseline, prior to vaccination) and day 14 by jugular puncture; and again at day 21 by intra-cardiac puncture (just prior to euthanasia).

Fluzone-specific IgG was assessed in serum derived from all the taken blood samples using an ELISA developed in our laboratory. Briefly, flat-bottomed plates (Nunc, Rochester, N.Y.) were coated with dialyzed Fluzone™ vaccine at a 1:80 dilution in coating buffer [0.5M Carb/Bicarb Buffer, pH 9.6] and incubated overnight at 4° C. Following incubation, wells were blocked with 10% Fetal Bovine Serum (FBS) in Phosphate Buffered Saline (PBS) for 1 hour at room temperature (RT). The wells were washed three times with PBS/0.05% Tween-20 prior to the addition of 50 µL of sera diluted in PBS/10% FBS and incubated for 1 h at 37° C. Plates were washed again with PBS/Tween followed by the addition of goat anti-pig IgG conjugated to peroxidase (Bethyl Laboratories, Montgomery, Tex.) at a dilution of 1:400 in PBS/10% FBS for 1 h at 37° C. TMB (BD Biosciences, San Jose, Calif.) and incubated for 20 minutes at RT, followed by addition of 50 µL of 2N sulfuric acid. Absorbance at 450 nm for each well was measured with a SpectraMax M2e (Molecular Devices, Sunnyvale, Calif.). Samples of positive stock serum, comprising known amounts of Fluzone-specific IgG, were included on each plate in dilutions ranging from 1:2,000-1:80,000 and used to provide a standard curve for Fluzone-specific IgG concentration. Fluzone-specific IgG were expressed in arbitrary units calculated from the linear portion of the standard curve.

Total IgG and IgM concentrations in serum derived from the taken blood samples were measured using commercially available ELISA kits (Bethyl Laboratories, Montgomery, Tex.).

1.4 Statistical Analysis of Serum Antibody Concentrations

Circulating levels of immunoglobulin (FZ-specific IgG, Total IgG and Total IgM) were tested using repeated measures analysis, with polynomial contrasts for time within SAS (Version 9.2, SAS Institute Inc., Cary, N.C.). The analysis was performed in the complete data set and separately within the vaccinated and non-vaccinated groups. Measurements performed on blood samples taken on day 21 were tested using Proc Mixed analysis with litter of origin as random variable. Main effects analyzed were diet, vaccination and the interaction of diet and vaccination. Interaction was removed from the model when it was not significant. Data was reported as means±SD. Comparisons with $p<0.05$ were deemed significant, and those with $p<0.1$ as a trend.

1.5 Tissue Sample Collection from Animal Test Population.

Prior to euthanasia at 21 days postpartum, piglets were sedated with Telazol (7 mg/kg body weight, IM, Fort Dodge Animal Health, fort Dodge, Iowa) and peripheral blood was collected in heparin laced vacuum tubes through intra-cardiac puncture. Piglets were then euthanized by injection of sodium pentobarbital (72 mg/kg body weight, Fatal Plus, Vortech Pharmaceuticals, Dearborn, Mich.). The small intestine was excised from the pyloric sphincter and ileocecal valve and total intestinal length was measured, and the intestine was cut at 10% and 85% from the proximal end to give 3 segments corresponding to the duodenum, jejunum and ileum, respectively. Spleen and Heal mesenteric lymph node (MLN) samples were also excised for isolation of mononuclear cells.

1.6 Isolation of Peripheral Blood Mononuclear Cells (PBMC)

Peripheral blood was initially diluted with RPMI-1640 (2:1; Life Technologies, Grand Island, N.Y.), then layered onto Ficoll-Paque Plus (GE Healthcare, Piscataway, N.J.), and spun at 400×g for 40 min at 20° C. PBMCs were collected from the gradient interface and washed three times in wash buffer (Hanks Buffered Salt Solution, no Ca++, no Mg++, Life Technologies) supplemented with 2% Bovine serum albumin (BSA; Sigma-Aldrich, St. Louis, Mo.), 0.01M EDTA (Sigma-Aldrich), 50 µg/mL Gentamycin (Life Technologies), and 1000 U/mL Penicillin (10000 U/ml stock, Sigma-Aldrich) and 100 µg/ml Streptomycin (10 mg/mL stock, Sigma-Aldrich). Remaining red blood cells in the pellet were lysed with lysis buffer (0.15M of $NH_4Cl$, 10 mM $KHCO_3$, and 0.1 mM $Na_2EDTA$). PBMCs were suspended in RPMI-1640 supplemented with 10% FBS, 2 mM Glutamine, 50 µg/mL Gentamycin, 1 mM Sodium Pyruvate (Life Technologies), 20 mM HEPES (Life Technologies), and 20 mM 1000 U/mL Penicillin/100 µg/ml Streptomycin. The number of viable cells was assessed with Countess® Automated Cell Counter (Life Technologies). Cells were then use for phenotypic cell identification by flow cytometry or ex vivo cell stimulation.

1.6 Isolation of Total Immune Cells from Spleen and MLN

Spleen and MLN samples were placed into collection buffer (Hank's Balanced Salt Solution (HBSS), 50 µg/ml Gentamycin, 0.01M 4-(2-hydroxyethyl)-1-piperazineethanesulfonic acid (HEPES), 1000 U/ml Penicillin and 100 µg/mL Streptomycin) and washed three times with PBS (Life Technologies)+ antibiotics (50 µg/mL Gentamycin, 1000 U/ml Penicillin and 100 µg/mL Streptomycin). Tissues were then homogenized in HBSS and chopped using Gentle MACS (Miltenyi Biotech, Auburn, Calif.). The tissue homogenates were strained through a 100 µm (BD Falcon, San Jose, Calif.) followed by a 40 µm cell strainer (BD Falcon). The isolated cells were washed three times in wash buffer after lysis of the red blood cells and suspended in complete media (RPMI-1640, 10% FBS, 2 mM Glutamine, 50 µg/mL Gentamycin, 1 mM Sodium Pyruvate, 20 mM HEPES, and 20 mM 1000 U/mL Penicillin/100 µg/mL Streptomycin). The number of viable cells was assessed as described above.

1.7 Phenotypic Identification of PBMC and Total Immune Cells Isolated from MLN and Spleen The phenotypes of mononuclear subpopulations from peripheral blood, MLN and spleen were monitored by flow cytometry (BD™ LSRII, Biosciences) using a panel of fluorescein (FITC) or Phycoerythrin (PE)-labeled mAbs. T-lymphocytes were identified by mouse anti-pig CD4 (FITC, Clone 74-12-4) and mouse anti-pig CD8 (PE, Clone 76-2-11) antibodies (BD Biosciences). Ten µl of each antibody were added to $1 \times 10^6$ cells from each sample. Staining procedures took place on ice and samples were removed from light when possible. In brief, each well was blocked with 5% mouse serum (Southern Biotec) and 200 µg/mL purified mouse IgG (Invitrogen) for 5 min each. After centrifugation, CD3 was added to the wells and incubated for 20 min (50 µL: CD3:PE-Cy5) and centrifuged again. CD4:FITC and CD8:PE were added (10 µL each) and incubated for an additional 15 min until centrifuged. Cells were washed with PBS/1% BSA/0.1% sodium azide and then fixed with 2% paraformaldehyde. Cells were assessed using a LSRII flow cytometer (BD™, Biosciences). The percentage of T-cell subpopulations was determined using FlowJo 7.9 software (FlowJo, Ashland, Oreg.). CD3+ events were considered T-cells. CD3+CD4+CD8− events were considered T-helper cells, CD3+CD4-CD8+ and CD3+CD4+

CD8+ were considered cytotoxic T and memory T-cells respectively. CD3-CD4-CD8+ events were labeled Natural Killer cells.

1.7 Ex Vivo Stimulation of Peripheral Blood Mononuclear Cells and Spleen Cells:

Ex vivo stimulation assay was conducted as an indicator of the functional capacity of the immune system. A total of $2 \times 10^6$/mL mononuclear cells from blood and cells from spleen were plated in 96-well plates in a final volume of 200 µL culture medium (RPMI medium including 20% fetal calf serum, 2 mM L-glutamine, 100 µg/mL penicillin and 100 µg/mL streptomycin) for 72 h at 37° C. under 5% $CO_2$. Either 50 µl of a solution of 10 µg/mL Phytohemagglutinin (PHA), 50 µL of a solution of 0.8 µg/mL Lipopolysaccharide (LPS) or 18 µL of a solution of 180 µg/mL Fluzone™ were added to wells in the presence or absence of OPN (10 µL of 10 µg/mL). After the 72 hour incubation period, plates were centrifuged and supernatants were collected for measurement of cytokine secretion.

1.8 Measurement of Cytokine Secretion in by Ex Vivo Stimulated Cells:

Cytokine secretion was measured using commercially available kits for IL-10, IL-6 and IL-12/IL-23 p40 (R&D Systems, Minneapolis, Minn.). Briefly, 96-well plates were coated overnight at 4° C. with capture antibodies using concentrations recommended by the manufacturer. Plates were washed with 0.05% Tween in PBS and then blocked using 1% BSA in PBS for 1 hour at room temperature. After 3 washes with 0.05% Tween in PBS, 100 µL of undiluted supernatant was added to the wells and incubated for 2 hours at room temperature. Wells were washed again prior to the addition of the detection antibody diluted 1:180 in 1% BSA in PBS, and plate was incubated for 2 hours. Streptavidin-horseradish peroxidase conjugate solution was added to wells and incubated for 20 min, followed by the addition of TMB substrate reaction (OptEIA, BD Biosciences). After 20 min incubation, reaction was stopped with 50 µL of 2N $H_2SO_4$. Absorbance was measured in a plate reader at wavelength of 450 nm.

Figure 2:
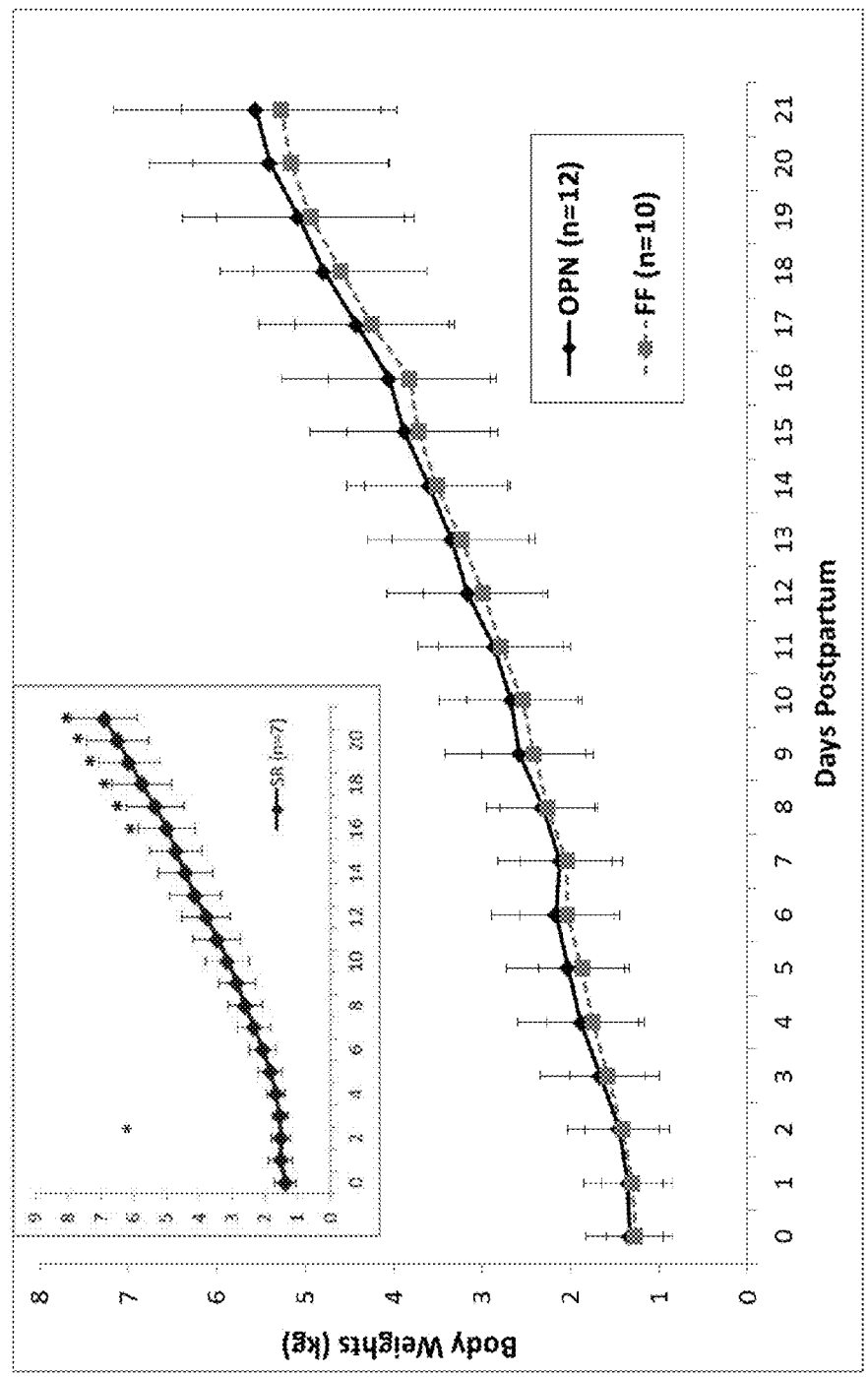
FIG. 2 Average daily body weight postpartum of piglets belonging to the dietary groups receiving sow milk replacer formula (FF; n=10) or formula supplemented with 140 mg/L osteopontin (OPN; n=12), and shown in the inset the sow-reared piglets (SR; n=7).

2. Results 2.1 OPN Supplement to Formula-Fed Piglets has No Effect on their Body Weight Gain Piglets in all groups demonstrated normal body weight gain. Supplementation of formula with OPN or vaccination did not affect piglet body weight gain (FIG. 2). Body weights in the SR group (inset in FIG. 2) were comparable to formula fed from birth through day 15, while by day 16 their body weights were greater than FF or OPN.

2.2 Fluzone™ Specific-IgGs in Formula-Fed Piglets is Enhanced by a Dietary OPN Supplement to Levels in Sow Reared Piglets.

Figure 3:
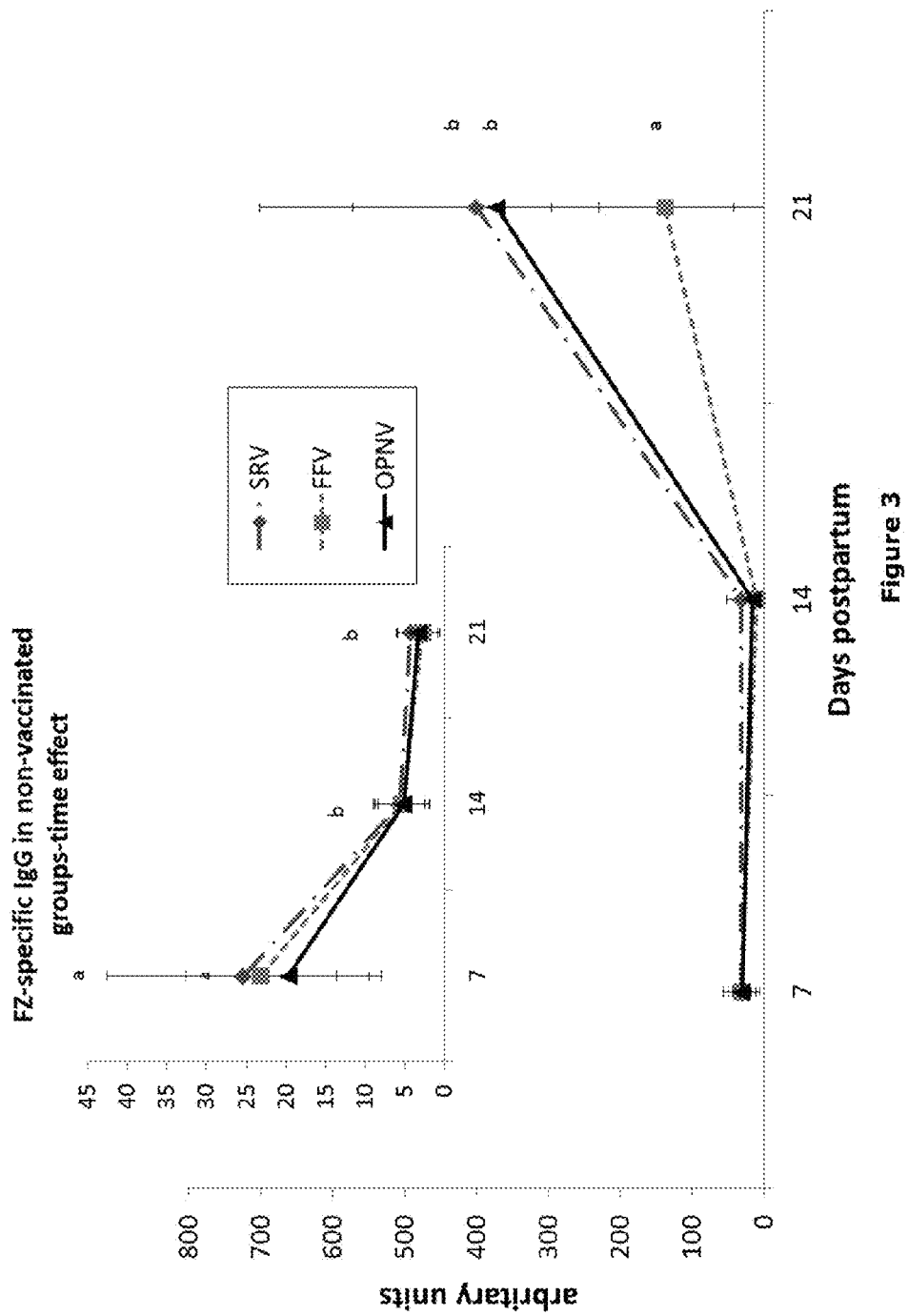
FIG. 3 Fluzone™-specific IgG titer in the serum derived from 7-, 14- and 21-day-old piglets measured by ELISA. Fluzone-specific IgG levels in non-vaccinated piglets are shown in the inset. Data are expressed as mean±SD. Different subscripts refer to statistical significance at p<0.05. Superscripts in non-vaccinated group refer to statistically significant time differences; superscripts in vaccinated graph indicate differences between dietary treatment groups at day 21.

Fluzone-specific IgG titer in the serum derived from 7, 14 and 21-day old piglets was measured by ELISA. A positive control sample was used as the standard curve for the calculation of the relative quantities of FZ-specific IgG, and the values are reported as arbitrary units (FIG. 3). Overall repeated measure statistics showed a vaccination (p=0.0005) and time effect (p=0.0001), but no dietary treatment effect. Further polynomial trend analysis of time effect showed significant linear and quadratic (p<0.05) contrasts. Post-hoc statistical analyses of the non-vaccinated group indicated that circulating FZ-specific IgG was generally low and was not affected by diet. However, FZ-specific IgG concentration decreased significantly (p<0.05) from day 7 to day 14 and 21. Vaccination had no impact on serum levels of FZ-specific IgG after the first dose of FZ. By day 21, after the booster dose given at day 14, animals from all 3 treatment groups responded to the FZ vaccine. FZ-specific IgG concentration in OPNV piglets was similar to SRV piglets, and both were significantly higher (p<0.05) than FFV piglets (measured levels in the 3 groups being 371±329, 400±171 and 137±157, respectively).

2.3 Total IgG and IgM Titer in the Serum of Vaccinated and Non-Vaccinated Piglets Declines Over Time.

Figure 4:
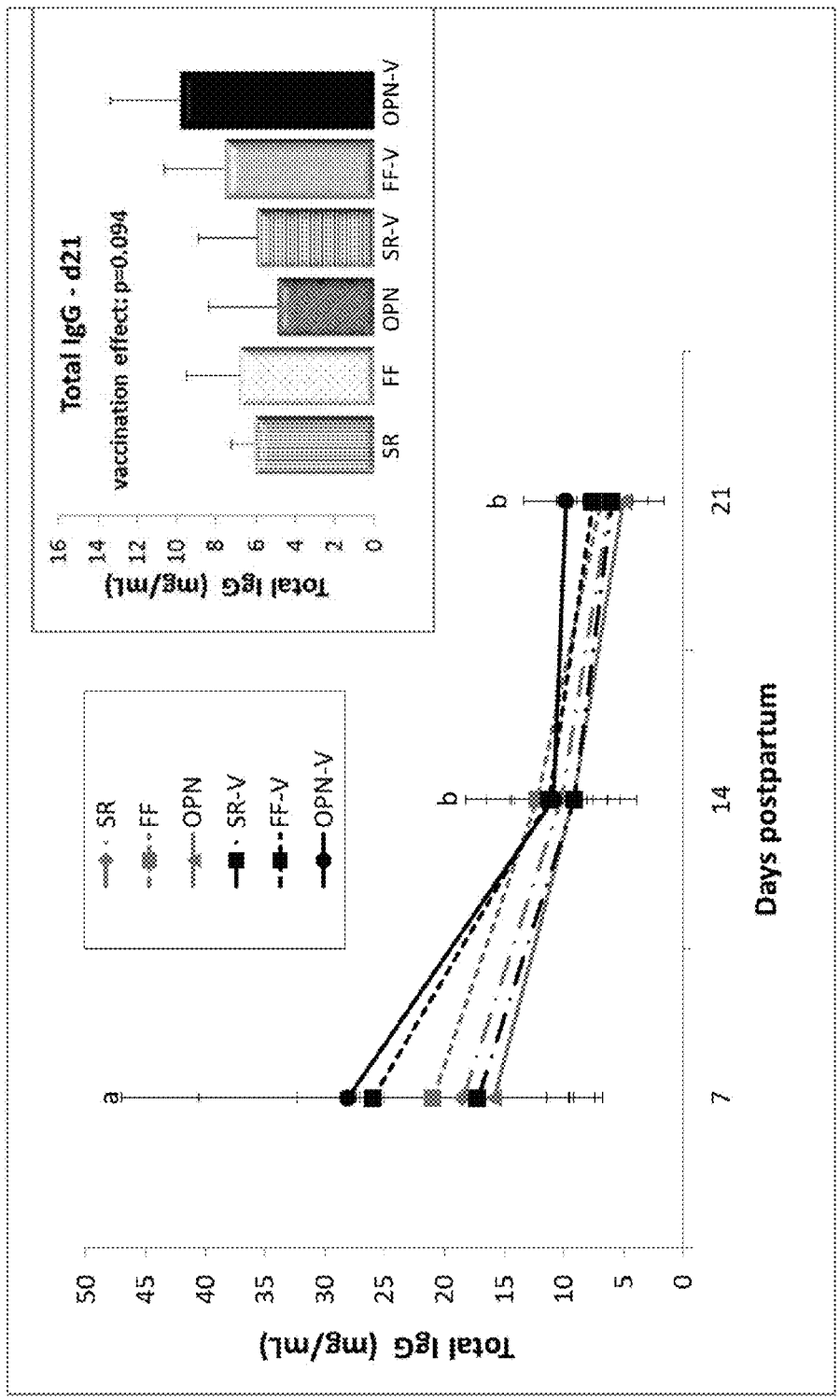
FIG. 4 Total IgG concentrations in serum of vaccinated and non-vaccinated piglets measured by ELISA. The serum was derived from piglet blood samples taken 7-, 14- and 21-days of age. Total IgG levels measured in samples taken at day 21 are shown in the inset. Data are expressed as mean f SD. Superscripts refer to statistically significant differences over time.
Figure 5:
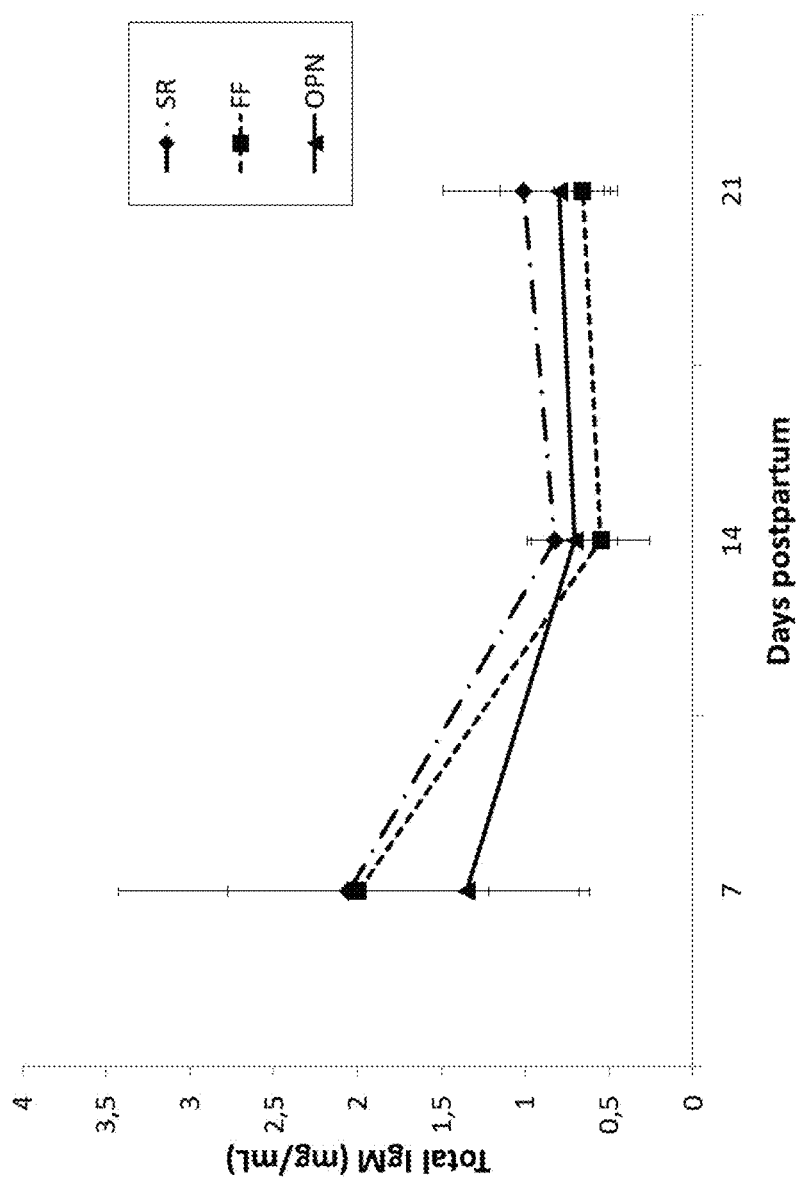
FIG. 5 Total IgM concentrations in serum derived from 7-, 14- and 21-day-old piglets measured by ELISA. Data are expressed as mean±SD. Superscripts refer to statistically significant differences over time.

Total IgG level in serum measured by ELISA (FIG. 4) was not affected by diet or vaccination. However, a steady decline in measured total IgG levels over time is statistically significant (p<0.01), with significant linear change after the repeated measure analysis (p<0.002). Proc mixed analysis at day 21 indicated a trend pattern (p=0.09) of higher total IgG levels in the vaccinated piglets when compared to non-vaccinated (7.5±2.5 and 5.9±2.7 mg/mL, respectively). Furthermore, vaccination increased total IgG levels in the OPN group by ~2-fold (96%), but the changes observed in the FF and SR piglets (0 and 10%, respectively) were rather small. This increase in total IgG levels reflects a better capacity to generate an adaptive immune response in piglets receiving a dietary OPN supplement. Total IgM concentration was not affected by diet or vaccination, but declined initially during the postpartum period (p<0.001; with linear and quadratic contrasts at p<0.0001). FIG. 5 indicates total IgM levels after pooling data from non-vaccinated and vaccinated groups within each dietary treatment.

2.4 Diet and Vaccination Affected the Phenotypic Profile of Lymphocytes

Figure 6:
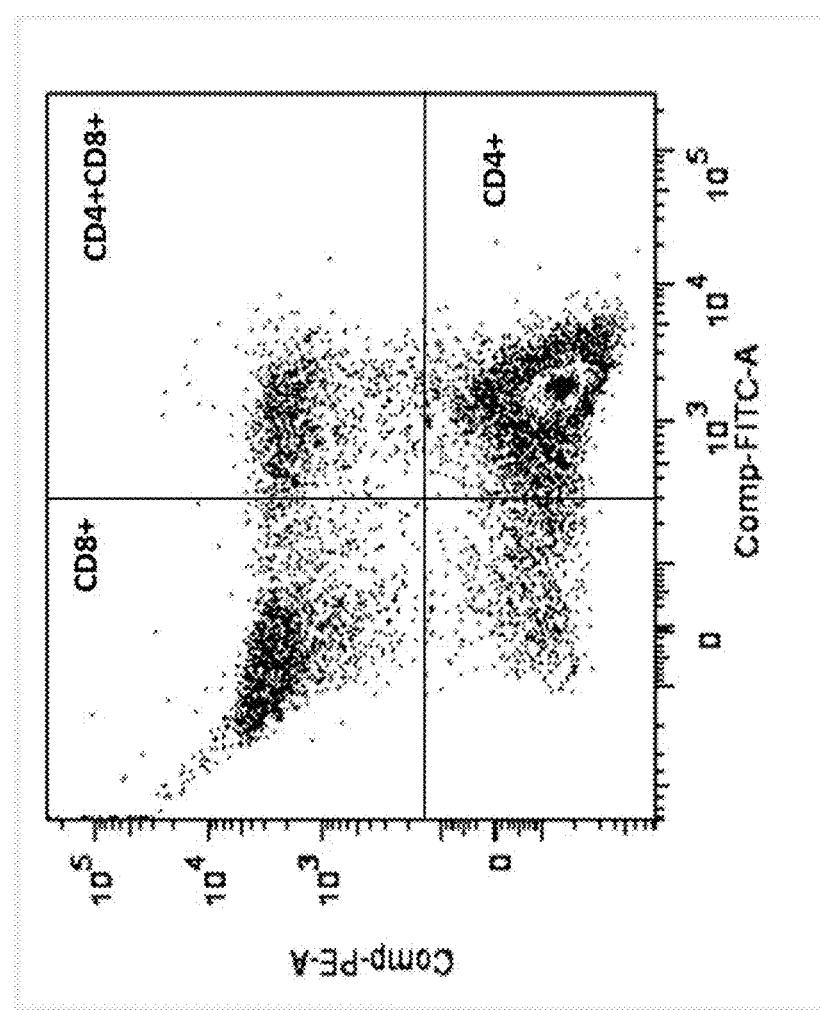
FIG. 6 Flow Cytometry scatter plot of PBMC T-lymphocyte populations stained for CD4 (clone 74-12-4) and CD8 (clone 76-2-11). The 4 quadrants plot the CD8+ lymphocytes (cytotoxic T cells having a CD3+CD4-CD8+ profile); CD4+ lymphocytes (T-helper cells having a CD3+CD4+CD8− profile), CD4+CD8+ lymphocytes (memory T-cells having a CD3+CD4+CD8+ profile).
Figure 7:
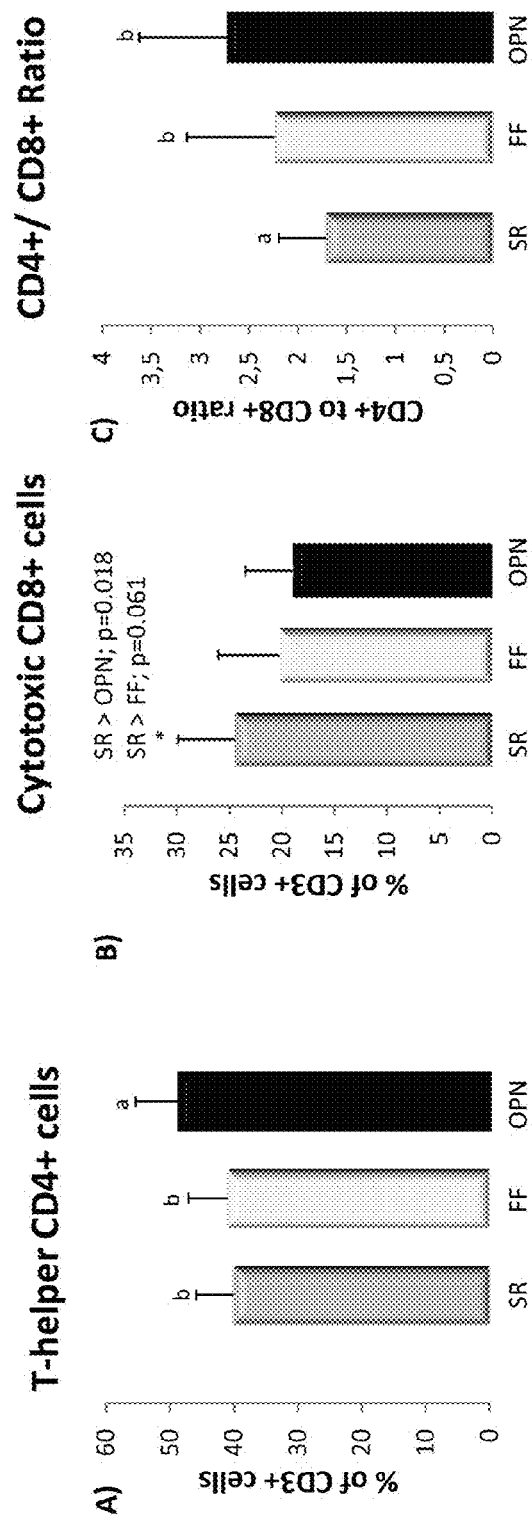
FIG. 7 Effect of diet on the abundance of T-helper CD4+ cells as (Panel A), cytotoxic CD8+ T-cells (Panel B) and on CD4+/CD8+ ratio (Panel C) in PBMC on day 21. Cell populations are expressed as a % of total CD3+ T-cells. Data are expressed as mean±SD and different superscripts indicate statistically significant differences at p<0.05. * indicates statistical trend at p<0.1.

The phenotypes of mononuclear subpopulations in spleen, PBMC and MLN samples taken at day 21 were identified by flow cytometry using a panel of fluorescein (FITC) or phycoerythrin (PE)-labeled mAbs. Cells were identified as cytotoxic-T cells, T-helper cells, double positive memory T-cells or Natural Killer cells (NKC) (FIG. 6) as described in Example 1.7. The phenotypic profile of lymphocytes in the PBMC and statistical analysis (with interaction diet*vaccination removed when non-significant) are presented in Table 1. T-helper (CD4+) cells, which have an active role in the adaptive immune responses, were responsive to diet, but not vaccination. T-helper cells were significantly higher in OPN than FF and SR animals (49.4% vs. 42.2% and 41.3%, respectively, FIG. 7A). Cytotoxic T cells (CD8+), important in host defense against cytosolic pathogens, were also not affected by vaccination, while diet effect showed a trend for difference. The differences of least square means analysis showed that the % of T-cytotoxic cells in the SR group was significantly higher than the OPN (p=0.018) and higher than FF at trend level (p=0.06) (FIG. 7B). To better understand the effect of diet on mononuclear cell population, the T-helper to T-cytotoxic ratio was calculated (FIG. 7C). The T-helper to T-cytotoxic ratio in PBMC's of OPN (2.73±0.89) and FF (2.24±0.90) piglets were significantly higher than that of the SR animals (1.71±0.48). This increase in T-helper to T-cytotoxic ratio indicates that the immune system is primed to make vaccine-specific antibodies in the vaccinated animals, in particular those piglets receiving an OPN supplemented diet.

The population of memory T-cells (double positive for CD4+ and CD8+) was significantly influenced by vaccination, while diet only showed a trend (p=0.052). Vaccination resulted in a 21% decrease in the % of CD3+ cells as CD4+CD8+ memory cells. The population of NK cells (CD4+CD3+CD8−) in PBMC changed after vaccination with a significant (p<0.05) increase from 14.8% in non-vaccinated animals to 23.7% in vaccinated animals, but there was no effect of diet.

TABLE 1

Distribution of lymphocytes in PBMC as %
CD3+ cells (T-cells) or CD3− cells (Natural Killer Cells).

| | Cytotoxic T cells (CD3+CD4−CD8+) | Memory T Cells (CD3+CD4+CD8+) | Helper T cells (CD3+CD4+CD8−) | NK cells (CD3−CD4−CD8+) |
|---|---|---|---|---|
| SR | 23.4 ± 1.17 | 21.3 ± 2.58 | 41.0 ± 7.62 | 20.0 ± 19.4 |
| FF | 19.8 ± 5.77 | 15.1 ± 4.67 | 39.0 ± 4.77 | 10.3 ± 4.04 |
| OPN | 16.9 ± 3.59 | 14.5 ± 4.10 | 49.5 ± 8.47 | 15.2 ± 6.31 |
| SRV | 26.0 ± 8.89 | 12.6 ± 3.34 | 38.9 ± 3.29 | 32.4 ± 14.6 |
| FFV | 20.7 ± 6.46 | 12.2 ± 4.47 | 43.0 ± 7.14 | 24.2 ± 15.1 |
| OPNV | 21.1 ± 4.56 | 13.2 ± 3.92 | 48.0 ± 5.0 | 19.0 ± 7.66 |
| Statistics | Diet: $p = 0.054$ Vaccination: N.S. | Diet: $p = 0.052$. Vaccination: $p < 0.01$ Diet * vac: $p < 0.04$ | Diet: $p < 0.01$ Vaccination: N.S. | Diet: N.S. Vaccination: $p < 0.03$ |

Data are expressed as mean ± SD

Figure 8:
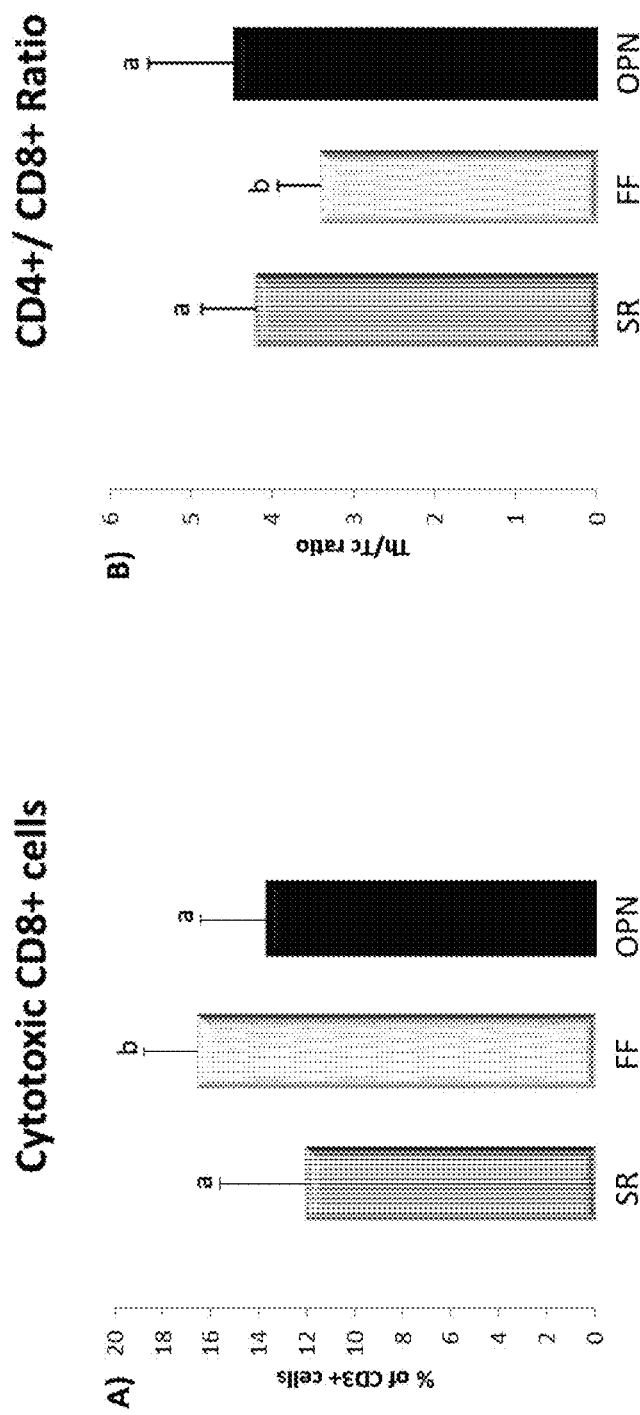
FIG. 8 Effect of diet on the abundance of cytotoxic CD8+ T-cells (Panel A) and on the CD4+/CD8+ T-cell ratio (Panel B) in MLN on day 21. Cell populations are expressed as a % of total CD3+ T-cells. Data are expressed as mean±SD and different superscripts indicate statistically significant differences at p<0.05. * indicates a statistical trend at p<0.1.
Figure 9:
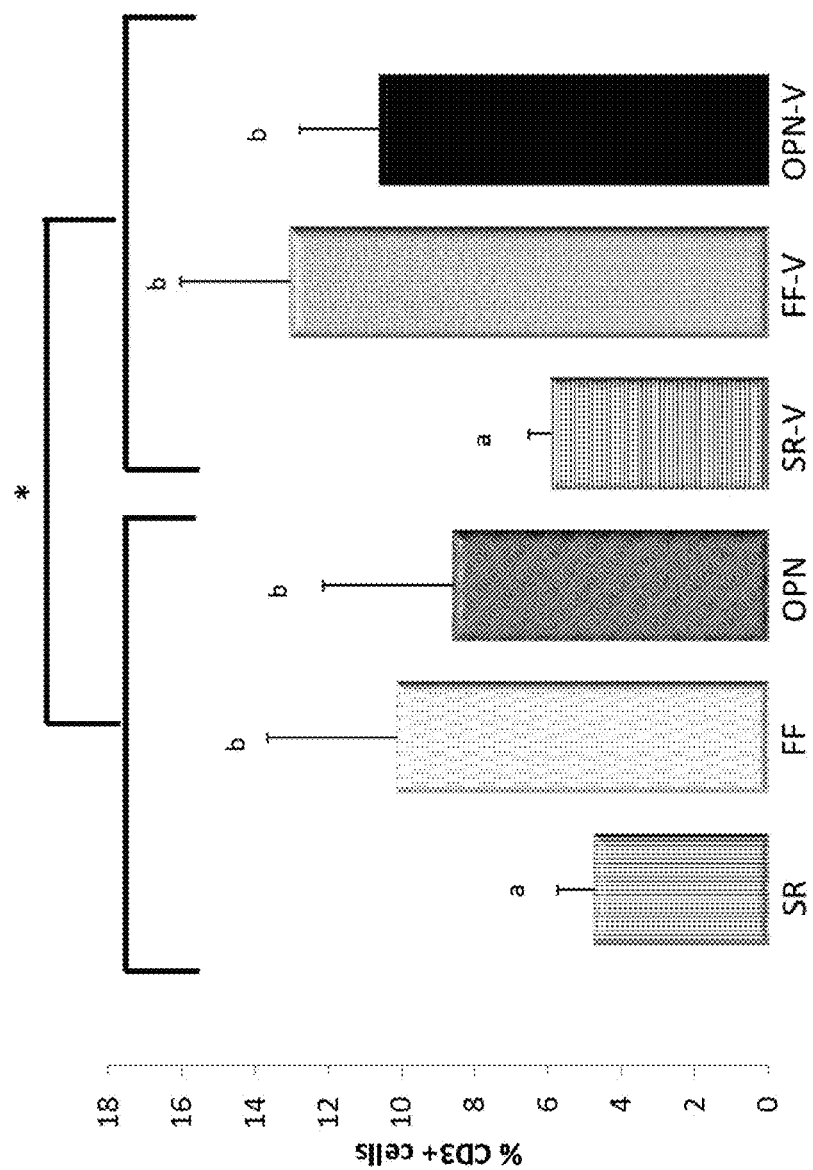
FIG. 9 Effect of diet on the abundance of memory (CD4+CD8+) T-cells in spleen on day 21. Cell populations are expressed as a % of total CD3+ T-cells. Data are expressed as mean±SD and different superscripts indicate statistical significant differences at p<0.05 for diet effect within vaccination group; * indicates statistical significance at p<0.05 for vaccination effect.

Immune cells were isolated from MLN as described) in Example 1.7 and cell populations identified as % of CD3+ and % of CD3− (Table 2). Vaccination had no significant impact in any of the MLN immune cells investigated. The number of T-cytotoxic cells in the OPN group (13.7%) closely resembled those of the SR group (12.0%), and they both differed significantly from FF animals (16.6%, FIG. 8A). Diet did not change the % CD3+ cells as T-helper, but it significantly (p<0.05) altered the population of T-cytotoxic cells. Similarly, OPN and SR T-helper/T-cytotoxic ratio values were comparable and significantly greater than for the FF (FIG. 8B). The increased ratio of CD4+/CD8+ cells seen in PBMC reflects an enhanced adaptive humoral response to vaccination in piglets receiving dietary OPN. NK cell population in the SR piglets were higher than both formula groups, but statistical significance was reached at trend level (p<0.06).

spleen were affected by vaccination but not by dietary treatment. The % of CD3+ as memory cells was influenced by diet and vaccination. Vaccination increased the population of memory cells, which are important in establishing the adaptive (humoral) response. Notably, both formula fed groups (OPN and FF groups) had significantly higher levels of memory cells than SR (FIG. 9). NK cells were significantly higher in the non-vaccinated SR animals when compared to all the other treatment groups. Vaccination did not affect NK levels in the spleen. The T-helper (CD4+)/T-cytotoxic (CD8+) ratio is also seems to increase in the spleen of vaccinated piglets, in particular those fed on SR or OPN, reflecting an induction of an adaptive humoral response.

TABLE 2

Distribution of MLN lymphocytes as %
CD3$^+$ (T-cells) or CD3$^−$ (Natural Killer) cells

| | Cytotoxic T cells (CD3+CD4−CD8+) | Memory T Cells (CD3+CD4+CD8+) | Helper T cells (CD3+CD4+CD8−) | NK cells (CD3−CD4−CD8+) |
|---|---|---|---|---|
| SR | 13.6 ± 3.09 | 14.6 ± 2.71 | 55.3 ± 5.47 | 3.1 ± 1.59 |
| FF | 16.3 ± 1.51 | 15.5 ± 3.19 | 53.9 ± 2.46 | 2.0 ± 0.69 |
| OPN | 14.4 ± 2.33 | 13.3 ± 4.36 | 60.3 ± 5.12 | 2.1 ± 0.82 |
| SRV | 10.5 ± 3.89 | 15.6 ± 9.39 | 61.7 ± 13.9 | 3.1 ± 0.86 |
| FFV | 16.8 ± 2.92 | 15.3 ± 5.15 | 57.2 ± 3.75 | 1.9 ± 0.51 |
| OPNV | 12.9 ± 3.15 | 17.3 ± 4.68 | 57.9 ± 3.82 | 1.9 ± 1.62 |
| Statistics | Diet: $p < 0.005$ Vaccination: N.S. | Diet: N.S. Vaccination: N.S. | Diet: N.S. Vaccination: N.S. | Diet: $p = 0.056$ Vaccination: N.S. |

Data are expressed as mean ± SD

The distribution of mononuclear cells isolated from spleen is shown in Table 3. T-helper and T-cytotoxic cells in

TABLE 3

Distribution of lymphocytes in spleen as % CD3$^+$
(T-cells) or CD3$^−$ (Natural Killer) cells.

| | Cytotoxic T cells (CD3+CD4−CD8+) | Memory T Cells (CD3+CD4+CD8+) | Helper T cells (CD3+CD4+CD8−) | NK cells (CD3−CD4−CD8+) |
|---|---|---|---|---|
| SR | 13.6 ± 3.09 | 4.7 ± 0.99 | 55.3 ± 6.98 | 10.7 ± 4.16[a] |
| FF | 13.0 ± 5.79 | 8.6 ± 4.02 | 46.0 ± 15.7 | 4.4 ± 1.10[b] |
| OPN | 13.9 ± 3.61 | 8.6 ± 3.52 | 44.9 ± 6.91 | 4.1 ± 2.70[b] |
| SRV | 10.5 ± 3.89 | 5.94 ± 0.58 | 61.7 ± 13.9 | 5.9 ± 0.89[b] |
| FFV | 12.5 ± 4.52 | 13.0 ± 2.97 | 48.2 ± 7.30 | 4.7 ± 1.47[b] |
| OPNV | 10.8 ± 2.43 | 10.6 ± 2.19 | 49.1 ± 5.87 | 5.8 ± 2.80[b] |

TABLE 3-continued

Distribution of lymphocytes in spleen as % CD3+ (T-cells) or CD3− (Natural Killer) cells.

| | Cytotoxic T cells (CD3+CD4−CD8+) | Memory T Cells (CD3+CD4+CD8+) | Helper T cells (CD3+CD4+CD8−) | NK cells (CD3−CD4−CD8+) |
|---|---|---|---|---|
| Statistics | Diet: N.S. Vaccination: $p < 0.05$ | Diet: $p < 0.01$ Vaccination: $p < 0.01$ | Diet: N.S. Vaccination: $p < 0.04$ | Diet: $p < 0.005$ Vaccination: N.S Diet * vac: $p < 0.02$ |

[1]Data are expressed as mean ± SD 2.5 Ex Vivo Stimulation and Cytokine Secretion by Isolated Immune Cells:

To assess the cellular immune responses of PBMC and spleen cells, the isolated cells were incubated for 72 hours with PHA, LPS or fluzone. Phytohaemagglutinin (PHA), a plant lectin, and lipopolysaccharide (LPS), a bacterial cell wall component, are mitogens that activate T-cells and B-cells, respectively. The activation of immune cells leads to secretion of cytokines. Interleukin 6 (IL-6), also known as interferon-beta 2, is a pleiotropic α-helical cytokine that is essential for the transition from acute inflammation to either acquired immunity or chronic inflammatory disease. Interleukin 10 (IL-10) is an anti-inflammatory Th2 cytokine, while interleukin-12 (IL-12) is a pro-inflammatory Th1 cytokine also known as natural killer cell stimulatory factor (NKSF) or cytotoxic lymphocyte maturation factor. The ex vivo cell culture was performed in the presence or absence of 10 µg/mL OPN in the culture media. The addition of OPN had no significant impact on the secretion of the cytokines assayed, thus the data from OPN-treated and untreated cells were pooled. Data with cytokine concentrations (pg/mL) for all treatments for PBMC and spleen are summarized in Tables 4 and 5, respectively. Statistically significant data were then pooled based on statistical differences and are shown in FIGS. 10-17.

Figure 10:
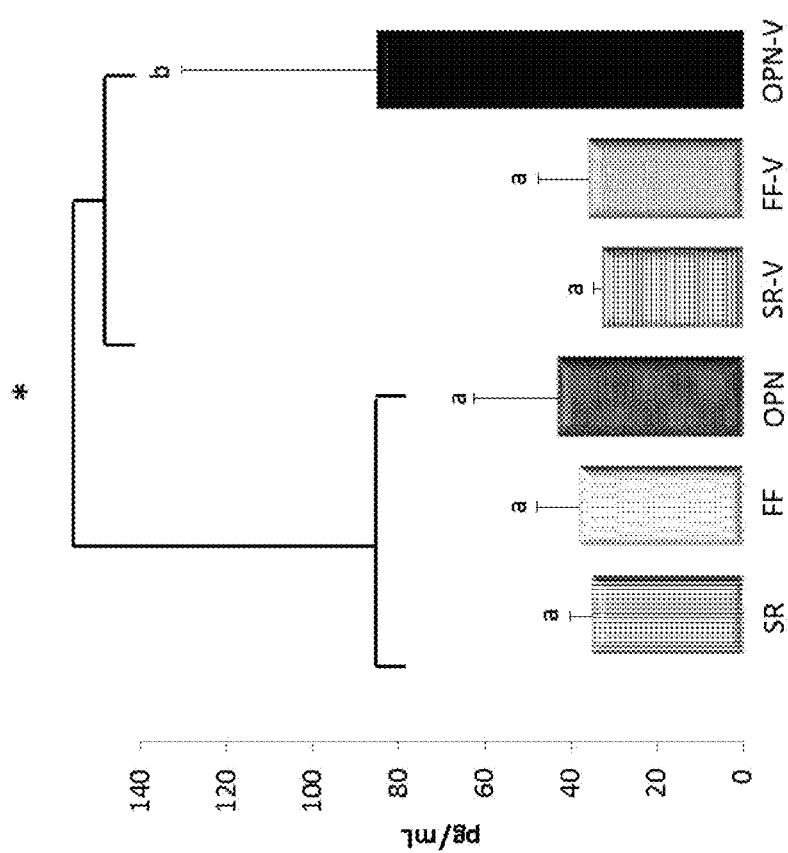
FIG. 10 IL-12 secretion by PBMC cells. PBMC cells were cultured ex vivo for 72 hours, conditioned media was collected and IL-12 was analyzed by ELISA. Data are expressed as mean±SD and different superscripts indicate statistical significant differences at p<0.05 for diet effect among treatment groups; * indicates statistical significance at p<0.05 for vaccination effect.
Figure 11:
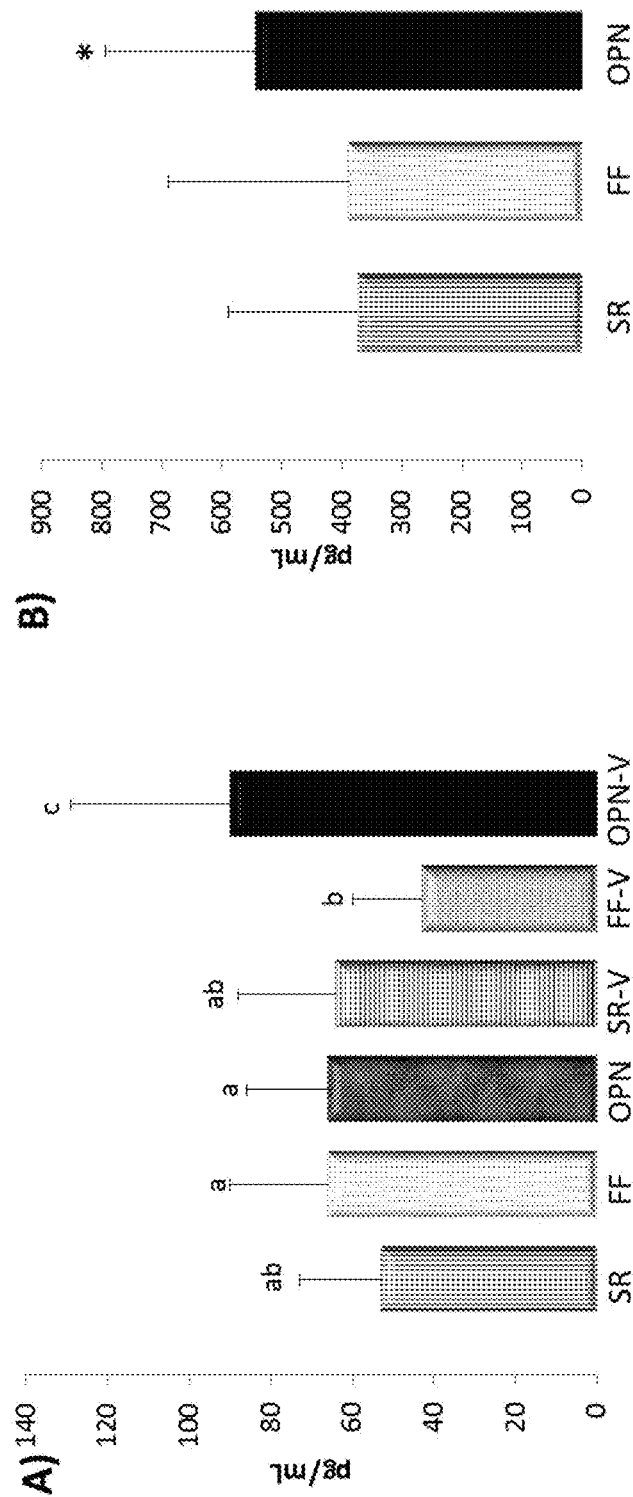
FIG. 11 Effects of phytohemagglutinin (PHA) stimulation on PBMC secretion of IL-12 (A) and IL-10 (B). PBMC cells were cultured ex vivo for 72 hours in the presence of PHA, conditioned media was collected and IL-10 and IL-12 were analyzed by ELISA. Data are expressed as mean±SD and different superscripts indicate statistical significant differences at p<0.05 for diet effect among treatment groups; * indicates a statistical trend at p<0.1 for diet effect.
Figure 12:
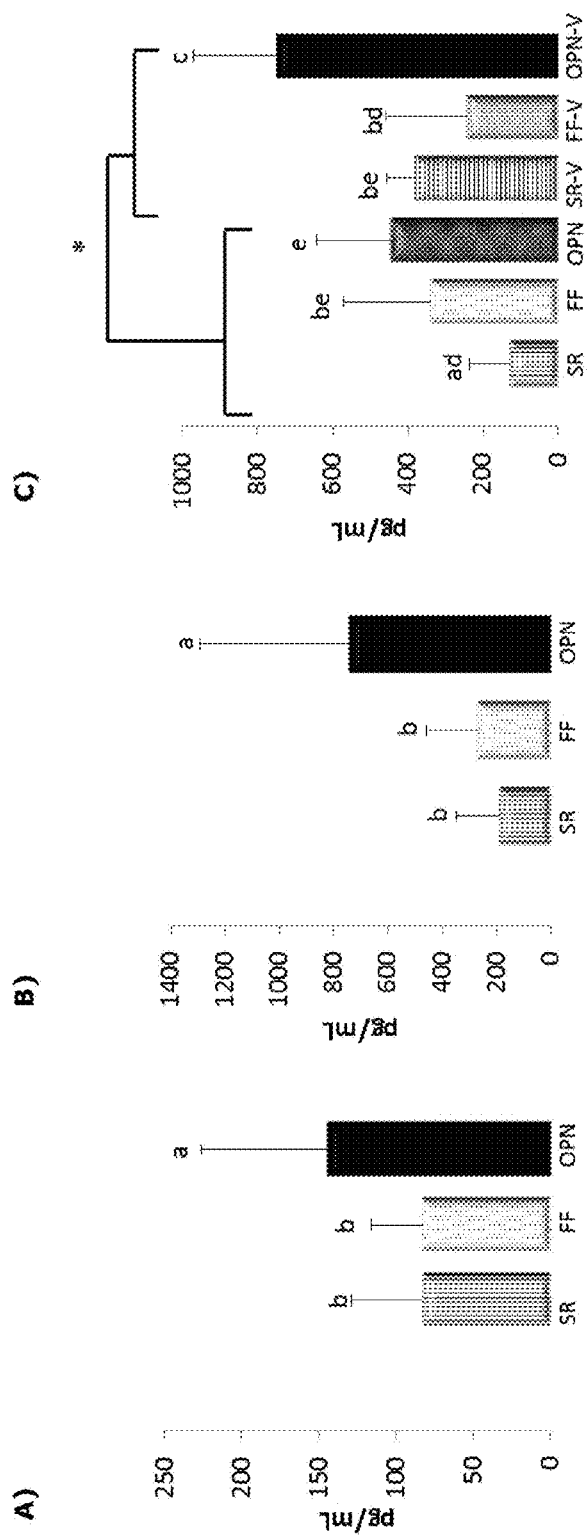
FIG. 12 Effects of lipopolysaccharide (LPS) stimulation on PBMC secretion of IL-12 (A), IL-6 (B) and IL-10 (C). PBMC cells were cultured ex vivo for 72 hours in the presence of LPS, conditioned media was collected and IL-6, IL-10 and IL-12 were analyzed by ELISA. Data are expressed as mean±SD and different superscripts indicate statistical significant differences at p<0.05 for diet effect among treatment groups; * indicates statistical significance at p<0.05 for vaccination effect.
Figure 13:
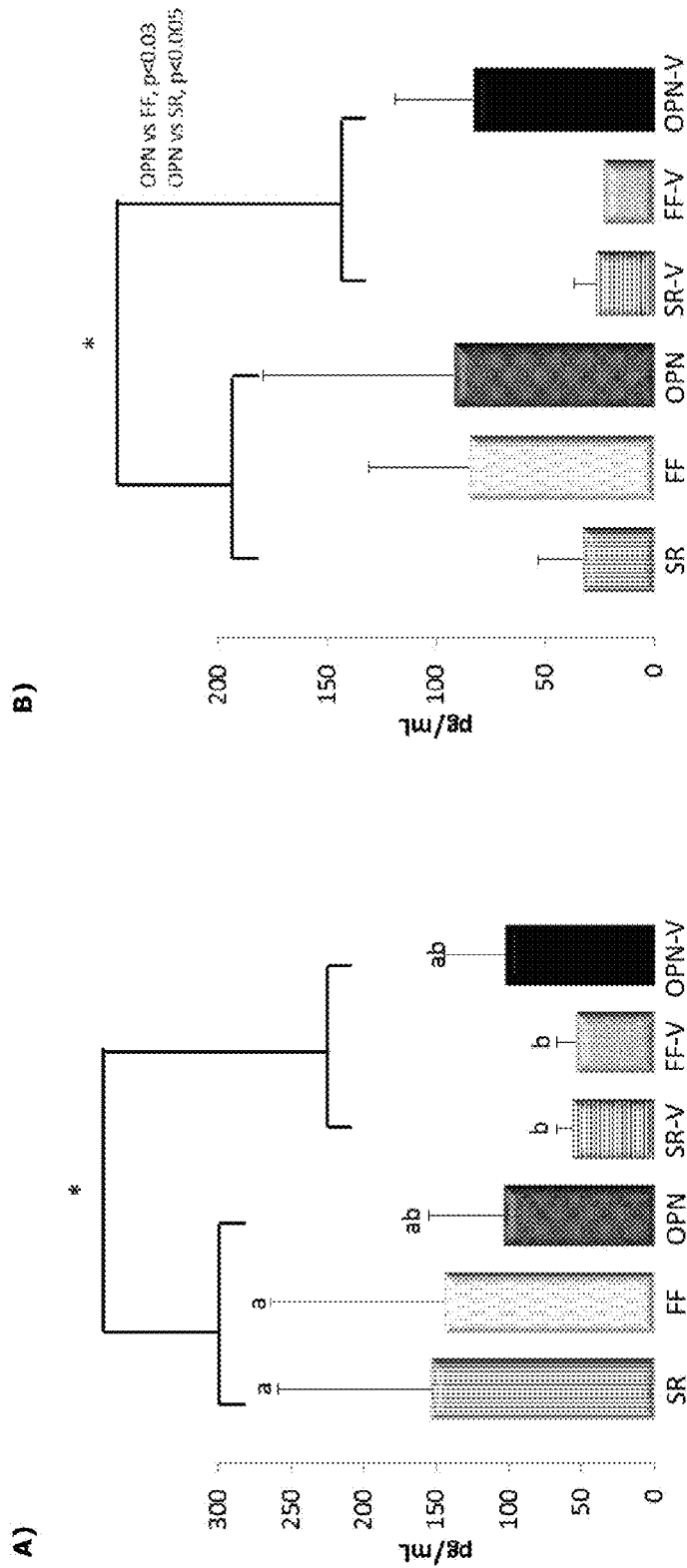
FIG. 13 Effects of Fluzone stimulation on PBMC secretion of IL-12 (A) and IL-10 (B). PBMC cells were cultured ex vivo for 72 hours in the presence of Fluzone, conditioned media was collected and IL-10 and IL-12 were analyzed by ELISA. Data are expressed as mean±SD and different superscripts indicate statistical significant differences at p<0.05 among treatment groups; * indicates statistical significance at p<0.05 for vaccination effect.
Figure 14:
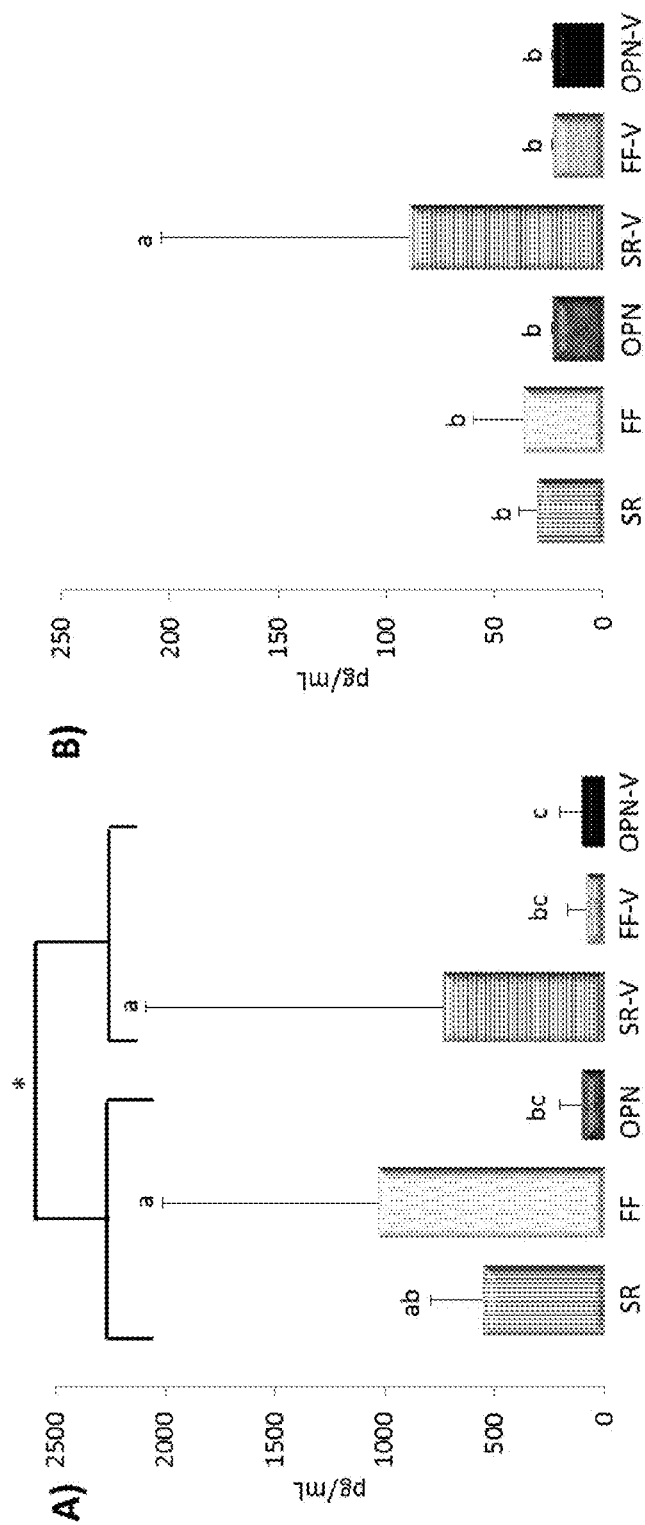
FIG. 14 IL-12 (A) and IL-10 (B) secretion by spleen cells. Spleen cells were cultured ex vivo for 72 hours, conditioned media was collected and IL-6, IL-10 and IL-12 were analyzed by ELISA. Data are expressed as mean±SD and different superscripts indicate statistical significant differences at p<0.05 for diet effect among treatment groups; * indicates a trend at p=0.07 for vaccination effect.
Figure 15:
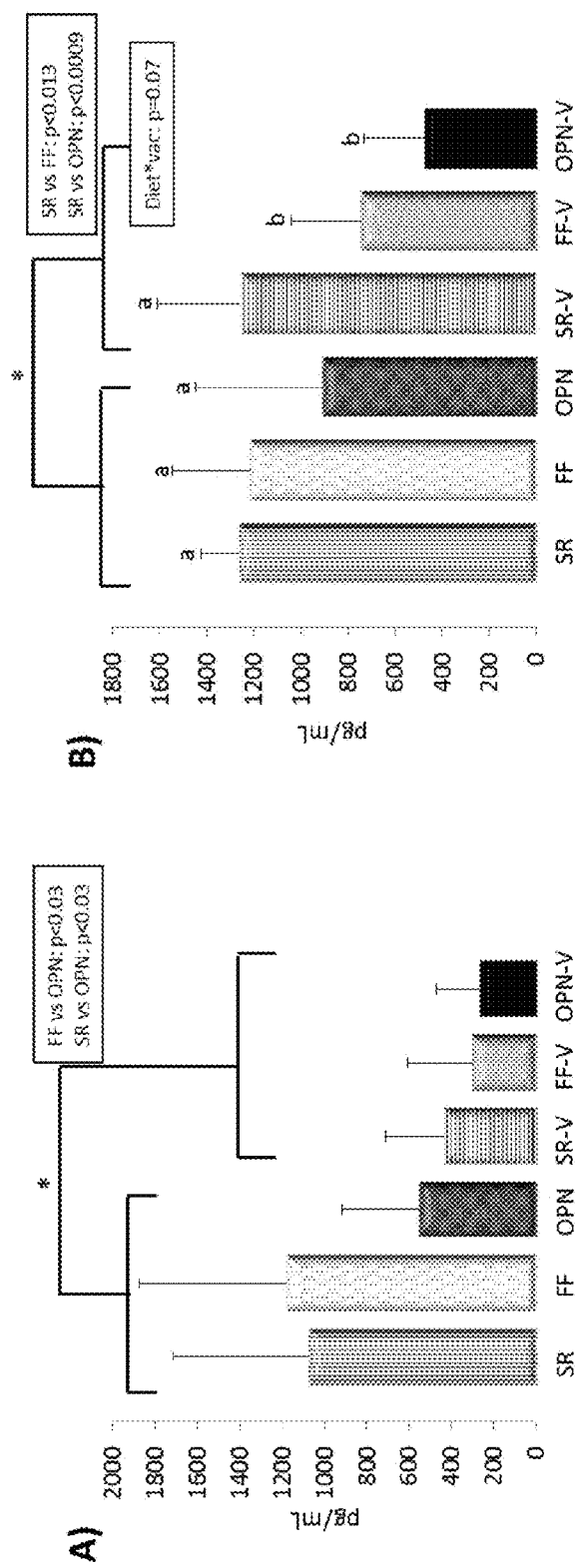
FIG. 15 Effects of phytohemagglutinin (PHA) stimulation on spleen secretion of IL-12 (A) and IL-10 (B). Spleen cells were cultured ex vivo for 72 hours in the presence of PHA, conditioned media was collected and IL-10 and IL-12 were analyzed by ELISA. Data are expressed as mean±SD; different superscripts indicate statistical trend at p=0.07 among treatment groups; * indicates statistical significant at p<0.05 for vaccination effect.
Figure 16:
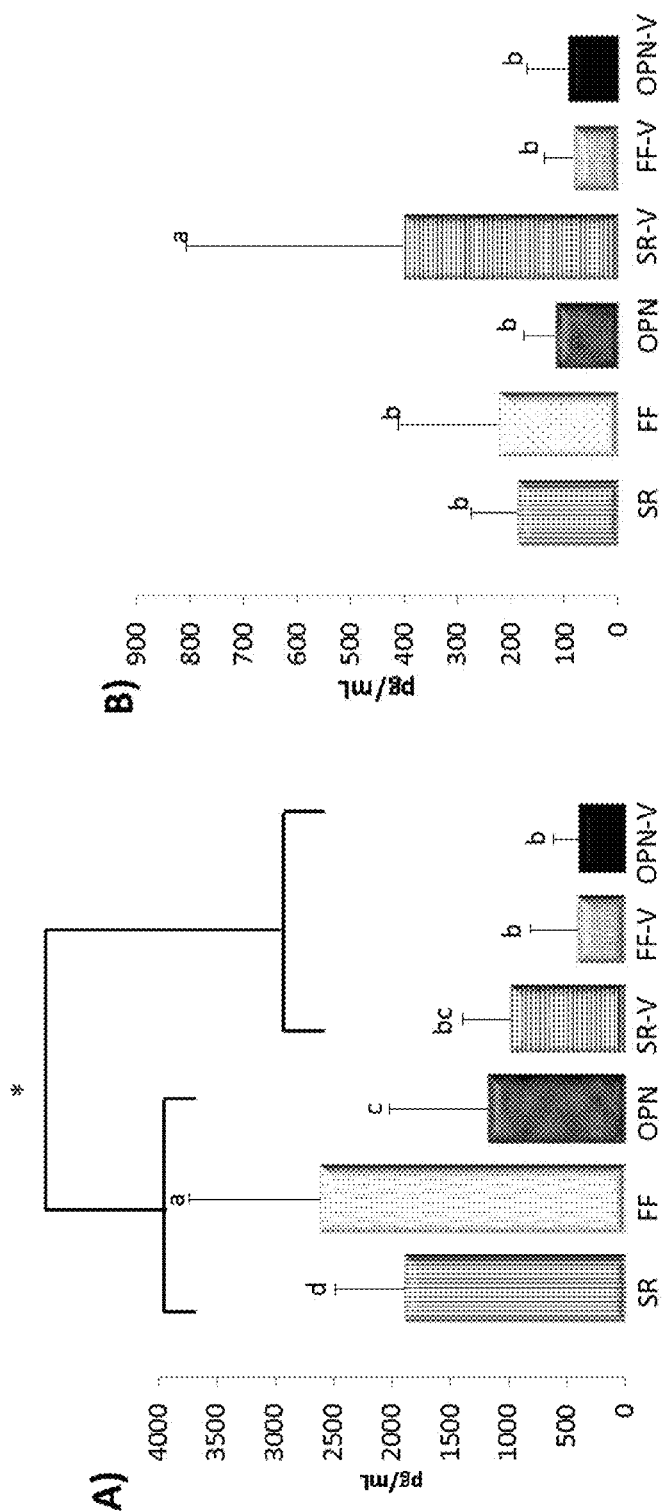
FIG. 16 Effects of lipopolysaccharide (LPS) stimulation on spleen secretion of IL-12 (A) and IL-10 (B). Spleen cells were cultured ex vivo for 72 hours in the presence of LPS, conditioned media was collected and IL-10 and IL-12 were analyzed by ELISA. Data are expressed as mean±SD and different superscripts indicate statistical significant differences at p<0.05 for diet effect among treatment groups; * Indicates statistical significant at p<0.05 for vaccination effect.

Peripheral Blood Mononuclear Cells:

In un-stimulated PBMC the concentration of IL-6 and IL-10 were below level of detection (Table 4). IL-12 was detected in the supernatant of un-stimulated cells and the effects of both diet and vaccination were statistically significant ($p<0.05$) (FIG. 10). IL-12 was highest in the PBMC of the OPNV group relative to all other treatment groups. PHA stimulation of cytokines in PBMC was not affected by vaccination. However, diet impact on IL-12 secretion was statistically significant with highest secretion observed in OPNV (FIG. 11A). IL-10 secretion tended to differ among the dietary groups, where cells obtained from OPN group tended to be higher than from SR and FF piglets (FIG. 11B).

The concentrations of IL-6 and IL-12 were significantly higher ($p<0.05$) in the LPS-stimulated PBMC originated from OPN fed piglets relative to SR and FF groups, regardless of vaccination (FIGS. 12A and B, respectively). Similar pattern was observed in the LPS stimulation of IL-10 secretion, where exposure to OPN resulted in higher concentration of IL-10. In addition, vaccination resulted in higher IL-10 levels in the OPN and SR groups (FIG. 12C).

The effect of Fluzone stimulation on IL-12 was vaccination-dependent, with a statistically significant interaction between diet and vaccination (FIG. 13A). Vaccination resulted in a decreased secretion of IL-12 in SRV and FFV, while the OPN group remained unchanged. IL-10 secretion in Fluzone-stimulated cells was higher in the OPN-fed group compared to SR and FF, while the vaccinated piglets had a lower concentration of IL-10 (FIG. 13B).

Figure 17:
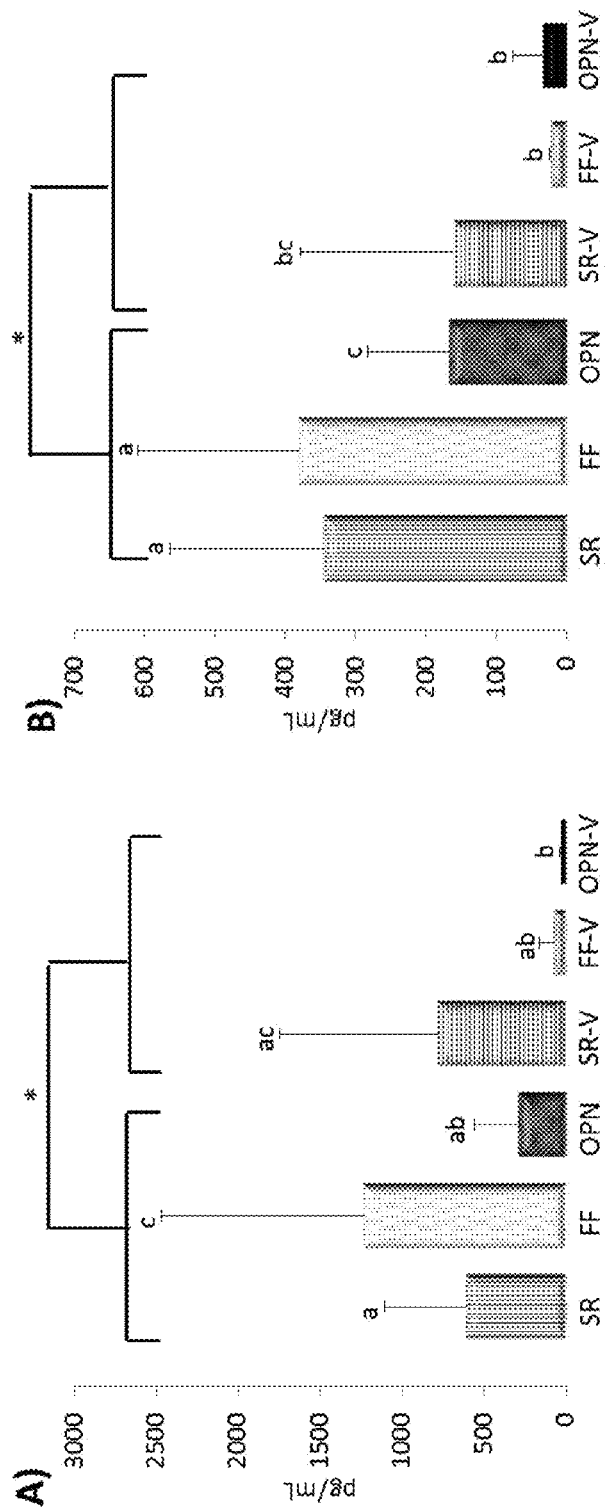
FIG. 17 Effects of Fluzone stimulation on spleen secretion of IL-12 (A) and IL-10 (B). Spleen cells were cultured ex vivo for 72 hours in the presence of Fluzone, conditioned media was collected and IL-10 and IL-12 were analyzed by ELISA. Data are expressed as mean±SD and different superscripts indicate statistical significant differences at p<0.05 for diet effect among treatment groups; * Indicates statistical significant at p<0.05 for vaccination effect.

Spleen Immune Cells:

Cells isolated from spleen were stimulated with PHA, LPS and Fluzone and cytokine production was measured in supernatant collected after 72 hours incubation (Table 5). Spleen cells did not produce any IL-6 in response to stimulus used in the study. IL-12, on the other hand, was found in the supernatant of un-stimulated cells (FIG. 14A). Cells from SR and FF groups secreted higher amounts of IL-12, whereas dietary OPN and vaccination tended ($p=0.07$) to decrease IL-12 concentration. IL-10 concentration in supernatants of un-stimulated cells was highest in the SRV group (FIG. 14B). IL-12 and IL-10 secretion by spleen cells in response to PHA stimulation was similar. Vaccination decreased the concentration of IL-12 (FIG. 15A) and IL-10 (FIG. 15B) when compared to levels found in the non-vaccinated groups. Furthermore, the OPN group had significantly lower levels of both cytokines than SR and FF groups. Similarly, IL-12 secretion in response to LPS was significantly higher in the supernatant of cells derived from non-vaccinated than vaccinated piglets ($p<0.05$) (FIG. 16A). Cells obtained from OPN group secreted the lowest amount of IL-12 relative to SR and FF groups. IL-10 secretion in LPS-stimulated cells was not affected by vaccination, but was higher in the SR group than the FF and OPN groups (FIG. 16B). Upon Fluzone stimulation, IL-12 and IL-10 secretion was lowest in the vaccinated group ($p<0.05$), and cells isolated from OPN animals secreted less IL-12 than SR and FF (FIG. 17).

In conclusion, when piglets receive a formula diet supplemented with OPN, their gastric cells are exposed to a constant concentration of OPN. This is in contrast to sow reared piglets where the level of OPN they receive will fall as the supply of sow colostrum is replaced by sow milk, and will be lower than the 140 mg/L provided in the OPN-supplemented formula diet. Piglets receiving the OPN-supplemented formula are characterized by immune cells (PBMCs) that secrete more IL-12 and IL-10, when incubated ex vivo both in the absence and in the presence of immune stimulants, when compared to cells derived from formula fed or sow reared piglets. This provides evidence that dietary OPN has the effect of priming PBMC cells to secrete IL-12 and IL-10. The capability of PBMCs from OPN-formula fed piglets, to secrete IL-12 (pro-inflammatory) and IL-10 (anti-inflammatory) upon stimulation with PHA (T-cell activation) and LPS (B-cell activation) suggests an immune mechanism geared towards immune balance.

Example 2

Clinical Trial with Lacprodan® OPN-10 Administered to Infants 2.1 Trial Design

A double-blind randomized clinical trial was performed in Shanghai, China to evaluate effects of adding bovine OPN to formula. Mothers chose to either breast- or formula-feed their infant from 1 to 6 months of age. The groups were as follows (n=60/group):
1) Breastfed infants
2) Infants fed regular formula (RF) with no added OPN (F0)
3) RF with added bovine OPN at ~65 mg OPN/L (F65)
4) RF with added bovine OPN at ~130 mg OPN/L (F130)
* Basal levels of OPN found in (un-supplemented) regular formula is ~15 mg OPN/L.

Anthropometry was registered monthly and venous blood samples were taken by veniopuncture at 1, 4 and 6 months of age. Hematology, immune parameters, plasma amino acids and blood urea nitrogen (BUN) were analyzed.

2.2 Trial Results

Figure 18:
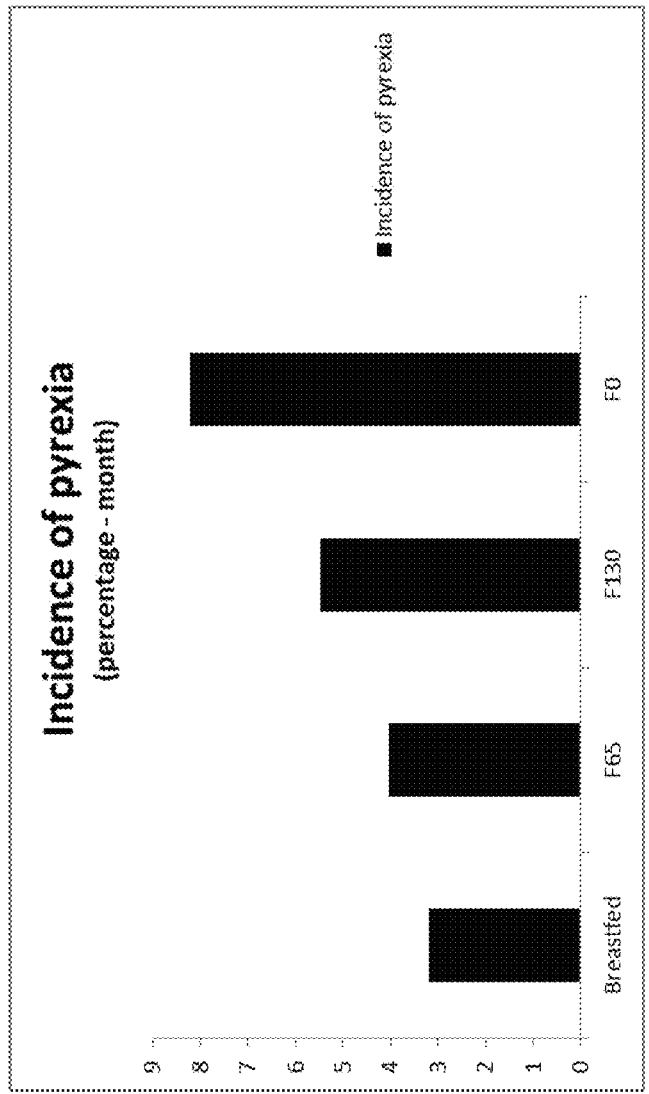
FIG. 18 Incidence of pyrexia in infants aged from 1 to 6 months of age when either 1) breastfed; 2) fed regular formula (RF) with no added OPN (F0); 3) RF with added bovine OPN at ~65 mg OPN/L (F65) and 4) RF with added bovine OPN at ~130 mg OPN/L (F130). Incidence is given as the percentage of time that infants belonging to each treatment group were recorded as having a fever during a period of one calendar month, (recorded time per calendar month values are averages of the values recorded over the period of the clinical trial).

The incidence of pyrexia in infants in response to infection (such as viral, bacterial, fungal or amoebal infection) was significantly increased in infants receiving regular formula (F0) as compared to breast fed infants (FIG. 18). The addition of OPN to regular formula in an amount of 65 mg OPN/L or 130 mg OPN/L reduced the high incidence of pyrexia seen when feeding with regular formula, down to levels closely approaching the low incidence levels seen in breast fed infants. The group of infants receiving regular formula (F0) was the only group to show a statistically significant increase in the incidence of pyrexia, when compared to breast fed infants.

REFERENCES

Albers et al. 2013 Monitoring immune modulation by nutrition in the general population: identifying and substantiating effects on human health. British 3 Nutrition 110(2): 1-22.

Bissonnette et al 2012; Proteomic analysis and immunodetection of the bovine milk osteopontin isoforms. Journal of Dairy Science, 95(2): 567-579, Plotkin, S A, 2008; Correlates of Vaccine-Induced Immunity. Vaccines 47:401-409

Sørensen et al 1995 Posttranslational modifications of bovine osteopontin: Identification of twenty-eight phosphorylation and three O-glycosylation sites; Protein Science 4: 2040-2049

The invention claimed is:

1. A method of enhancing immune resistance to an infectious disease in a mammal, the method comprising the steps of:
orally administering to the mammal an effective amount of mammalian milk osteopontin composition, wherein (1) the osteopontin composition comprises an enriched source of purified mammalian milk osteopontin having at least 80% purity, (2) the osteopontin composition is administered daily to the mammal in an amount of from about 0.05 mg/kg body weight to about 5.0 g/kg body weight, (3) the infectious disease is selected from the group consisting of: influenza, diphtheria, tetanus, whooping cough, polio, measles, mumps, rubella, tuberculosis, hepatitis B, meningitis C, rotavirus, human papilloma virus, influenza type a, influenza type b, pneumococcal infection and shingles, and (4) administration of the osteopontin composition enhances the immune resistance to infectious disease in the mammal.

2. The method of claim 1, where the purified mammalian milk osteopontin is at least about 80% to about 90%, or about 90% to about 95% pure.

3. The method of claim 2, wherein the mammalian milk osteopontin is about 95% pure, about 96% pure, about 97% pure, about 98% pure, about 99% pure or about 99.5% pure.

4. The method of claim 1, wherein the mammalian milk osteopontin comprises approximately 22% (w/w) full-length bovine milk osteopontin and approximately 65% (w/w) of a truncated bovine milk osteopontin isoform.

5. The method of claim 1, wherein the mammalian milk is selected from among bovine, goat, sheep, camel, buffalo, dromedary, llama and any combination thereof.

6. The method of claim 1, wherein the osteopontin is bovine and comprises an osteopontin polypeptide having an amino acid sequence of residues 17-278 of SEQ ID NO: 1; and an active truncated osteopontin polypeptide of 40 kDa derived from the OPN polypeptide by in vivo peptide bond cleavage at a position that is C-terminal to the RGD motif.

7. The method of claim 1, wherein the osteopontin is bovine and comprises an osteopontin polypeptide having an amino acid sequence of residues 17-278 of SEQ ID NO: 1; and an active truncated osteopontin polypeptide wherein the amino acid sequence is residues 17-163 of SEQ ID NO: 1.

8. The method of claim 1, wherein the osteopontin composition strengthens the humoral immunity in the mammal.

9. The method of claim 1, wherein the mammal is a human.

10. The method of claim 9, wherein the human belongs to an age group selected from the group consisting of: 0-5, 6-11, 12-18, 19-34, 35-44, 45-54, 55-64, 65-74, 75-84, and older than 84 years of age.

11. The method of claim 9, wherein the mammalian milk osteopontin composition is administered to the human as an oral dosage form.

12. The method of claim 11, wherein the oral dosage form contains from about 10 mg to about 800 mg of mammalian milk osteopontin.

13. The method of claim 11, wherein the oral dosage form contains from about 0.1 mg to about 10 g of mammalian milk osteopontin.

14. The method of claim 12, wherein the oral dosage form contains about 25 mg to about 500 mg of mammalian milk osteopontin.

15. The method of claim 9, wherein the mammalian milk osteopontin composition is administered to the human as a nutritional supplement.

16. The method of claim 14, wherein the nutritional supplement contains mammalian milk osteopontin in the range of 0.01-90% (w/w).

17. The method of claim 1, wherein the immune resistance to an infectious disease in a mammal is induced by vaccination.

18. A method of preventing or treating an infectious disease in a mammal, the method comprising:
orally administering an effective amount of a vaccine and a mammalian milk osteopontin composition comprising an enriched source of purified mammalian milk osteopontin having at least 80% purity, wherein administration of the osteopontin composition enhances the immune resistance induced by the vaccine to prevent or treat an infectious disease selected from the group consisting of: influenza, diphtheria, tetanus, whooping cough, polio, measles, mumps, rubella, tuberculosis, hepatitis B, meningitis C, rotavirus, human papilloma virus, influenza type a, influenza type b, pneumococcal infection and shingles.

19. The method of claim 18, where the purified mammalian milk osteopontin is at least about 80% or about 80% to about 90%, about 90% to about 95% pure.

20. The method of claim 18, wherein the purified mammalian milk osteopontin is about 95% pure, about 96% pure, about 97% pure, about 98% pure, about 99% pure or about 99.5% pure.

21. The method of claim 18, wherein the mammalian milk osteopontin composition strengthens the humoral immunity in the mammal.

22. The method of claim 18, wherein the osteopontin is selected from among bovine, goat, sheep, camel, buffalo, dromedary, llama, and any combination thereof.

23. The method of claim 18, wherein the osteopontin is bovine and comprises an osteopontin polypeptide having an amino acid sequence of residues 17-278 of SEQ ID NO: 1 and an active truncated osteopontin polypeptide of 40 kDa derived from the OPN polypeptide by in vivo peptide bond cleavage at a position that is C-terminal to the RGD motif.

24. The method of claim 18, wherein the osteopontin is bovine and comprises an osteopontin polypeptide having an amino acid sequence of residues 17-278 of SEQ ID NO: 1; and an active truncated osteopontin polypeptide wherein the amino acid sequence is residues 17-163 of SEQ ID NO: 1.

25. The method of claim 18, wherein the osteopontin composition is for oral administration prior to; concurrently with; or subsequent to vaccination of the mammal, or a combination thereof.

26. The method of claim 18, wherein the mammal is a human.

27. The method of claim 26, wherein the human belongs to an age group selected from the group consisting of: 0-5, 6-11, 12-18, 19-34, 35-44, 45-54, 55-64, 65-74, 75-84, and older than 84 years of age.

28. The method of claim 26, wherein the human is administered about 0.05 mg/kg body weight to about 5.0 g/kg body weight of mammalian milk osteopontin composition daily.

29. The method of claim 26, wherein the mammalian milk osteopontin composition is administered to the human as an oral dosage form.

30. The method of claim 29, wherein the oral dosage form contains from about 0.1 mg to about 10 g of mammalian milk osteopontin.

31. The method of claim 29, wherein the oral dosage form contains from about 10 mg to about 800 mg of mammalian milk osteopontin.

32. The method of claim 29, wherein the oral dosage form contains about 25 mg to about 500 mg of mammalian milk osteopontin.

* * * * *